(12) United States Patent  
Garry

(10) Patent No.: US 6,670,466 B1  
(45) Date of Patent: Dec. 30, 2003

(54) HUMAN ENDOGENOUS RETROVIRUS IN BREAST CANCER

(75) Inventor: Robert F. Garry, New Orleans, LA (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 27 days.

(21) Appl. No.: 10/018,865

(22) PCT Filed: Jun. 30, 2000

(86) PCT No.: PCT/US00/18279

§ 371 (c)(1),  
(2), (4) Date: Dec. 19, 2001

(87) PCT Pub. No.: WO01/00829

PCT Pub. Date: Jan. 4, 2001

Related U.S. Application Data

(60) Provisional application No. 60/141,626, filed on Jun. 30, 1999.

(51) Int. Cl.[7] .................................................. C07H 21/04
(52) U.S. Cl. ........................ 536/23.72; 435/5; 435/6; 435/7.92; 435/320.1; 435/455; 435/330; 435/331; 435/332; 435/339.1; 435/975; 436/516; 424/187.1; 424/207.1; 530/350; 530/388.35; 530/387.9; 530/388.8; 530/389.4; 530/389.7; 530/826
(58) Field of Search .................... 536/23.72; 435/320.1, 435/455, 330, 331, 332, 339.1, 5, 6, 7.92, 975; 436/516; 530/350, 388.35, 387.9, 388.8, 389.4, 389.7, 226; 424/187.1, 207.1

(56) References Cited

U.S. PATENT DOCUMENTS 5,686,247 A  11/1997  Holland et al.
6,040,146 A   3/2000  Pogo et al.

FOREIGN PATENT DOCUMENTS

WO    WO97/17470    5/1997

OTHER PUBLICATIONS

Wang et al., *Clinical Cancer Research* , vol. 4, pp. 2565–2568 (Oct. 1998).

Wang et al., *Cancer Research* , vol. 55, pp. 5173–5179 (1995).

Faff et al., *Journal of General Virology* , vol. 73, pp. 1087–1097 (1992).

Redmond et al., *The EMBO Journal*, Vol 2, pp. 125–131 (1982).

*Primary Examiner*—Jeffrey Stucker  
(74) *Attorney, Agent, or Firm*—Howrey Simon Arnold & White, LLP

(57) ABSTRACT

The present invention is related to mammary tumor virus (MTV). MTV represents a group of retroviruses which possess very high homology to mouse mammary tumor virus (MMTV), a virus known to cause neoplastic mammary disease in mice. As described herein, MTV's have been identified in human, cat, and Rhesus macaque. The present invention specifically provides for recombinant nucleic acids and polypeptides derived from these MTV's as well as methods for using these biological molecules.

26 Claims, 3 Drawing Sheets

HUMAN ENDOGENOUS RETROVIRUS IN BREAST CANCER

This application is a §371 national stage filing of PCT/US00/18279, filed Jun. 30, 2000 (published in English on Jan. 4, 2001 as WO 01/00829) and claiming priority to U.S. Ser. No. 60/141,626 filed Jun. 30, 1999, the entire text of which is specifically incorporated herein by reference.

BACKGROUND OF THE INVENTION

1. Field of the Invention

The present invention relates to compositions and methods for the detection, prognostic evaluation, and treatment of oncogenic disorders, particularly breast cancer.

Specifically, the instant invention provides for compositions, useful for identifying and treating disorders related to newly identified endogenous retroviruses which are present in a subset of humans, cats, and nonhuman primates.

2. Technical Problem Addressed by the Invention

Mutations in Known Susceptibility Genes do not Account for all Breast Cancer Breast cancer (BC) is one of the leading causes of cancer death among women. The as induction of BC is thought to involve the interplay of several factors, including the genetic, hormonal, immunological and physiological status of the host, as well as dietary habits and exposures to chemicals, radiation or infectious agents. It is now clear that variations of several genes, including BRCA-1 and BRCA-2, can result in greatly increased risks for development of BC. However, defects in known BC susceptibility genes account for only about 5% of BC, the so-called familial cases (Armstrong et al., 2000; Gayther et al., 1998).

As with other types of cancer, the possibility that a virus is etiologically involved in sporadically occurring BC has not been eliminated. Consequently, there has long been a need to determine which, if any viruses are causally linked to the development of BC. The identification of such a virus would likely provide invaluable aid in the following areas BC medicine: prevention, diagnosis, determination of prognosis, and treatment.

3. Description of Related Art

Retrovirus Induction of Breast Cancer in Mice

Mouse mammary tumor virus (MMTV), a B-type retrovirus, was discovered during studies of hereditary cancer in mice at the Jackson Laboratories in the 1930's (Bittner, 1936). As the prototype of slow-transforming retroviruses, MMTV has been definitively shown to cause BC in mice. Prior studies established that MMTV is transmitted both in the gerinline as endogenous proviruses and exogenously via milk. As endogenous elements MMTV proviruses follow patterns of Mendelian inheritance, as other sequences in the genome (Cohen et al., Cell,1979; Cohen and Varmus, 1979, 1980; Traina et al., 1981; Traina-Dorge and Cohen, 1983; Traina-Dorge el al., 1985; Varmus et al., 1978). Horizontal transmission of MMTV typically occurs by infection of mouse pups by MMTV virions present in the milk of infected dams. Thus, it is possible to transmit MMTV to mice by foster feeding. 30 or more unique proviral integration sites for endogenous MMTV have been identified. However, some wild mice do not carry any endogenous MMTV proviruses (Cohen and Varmus, 1979; Cohen et al, 1982). This result suggests that the many endogenous MMTV proviruses are relatively recent additions to the mouse genome. The most likely explanation is that MMTV entered the germline of certain mice (but not others) on multiple occasions after the evolutionary splits among the various species and subspecies of the genus Mus. Certain endogenous MMTV can be activated by hormones to form infectious virions capable of inducing mammary carcinomas after long latency periods. Most endogenous MMTV proviruses are defective and do not encode for infectious virions.

Roles of MMTV Genes and Cellular Genes in Oncogenesis

The MMTV Orf protein can function as a superantigen (SA). When expressed in the thymus during fetal/early development it can mediate complete or incomplete deletion of SA-reactive T-cells. SA expression is required to activate B-cells targets of MMTV in the gut-associated lymphoid tissue of nursing pups. Complete deletion of the SA responsive clones thus renders the mice resistant to MMTV infection in the gut and thereby leads to a low incidence of MMTV-induced tumors. On the other hand, in mice with only partially deleted responsive clones of lymphoid cells the SA activation stimulates expansion of the targets and spread of MMTV. As female infected animals reach puberty, estrogenic hormones drive expression of the MMTV long terminal repeat (LTR) through its hormone response element (HRE). This permits production and assembly of MMTV and spread of the virus to other hormonally-sensitive tissues, including the breast and ovaries. Integration of MMTV LTRs adjacent to certain cellular genes, such as the proto-oncogenes Int, Wnt and Fgf, can increase expression of these genes resulting in BC and other cancers.

The molecular genetic interactions between MMTV, the immune system of its murine host, and the breast and other hormonally-sensitive cells malignantly transformed by this retrovirus have been extensively studied. MMTV promotes mammary gland cancer in mice by insertional mutagenesis (Varmus et al., 1978; Varmus, 1985). MMTV proviral LTR elements direct steroid hormone-dependent transactivation of various cellular oncogenes including Wnt, Fgf and Int thereby promoting clonal expansion of tumor cells (Shackleford and Varmus, 1987, Shackleford et al, 1993; Jakobovits et al., 1986; Nusse, 1991; Nusse et al.,1985). For productive, persistent infection and completion of its replication cycle, MMTV must contain a superantigen and interact with a functional host immune system (Golovkina et al., 1995; Luther and Acha-Orbea, 1996; Coffin, 1992).

The Search for a Human Breast Cancer Virus

The discovery of the oncogenic MMTV has prompted many investigators to explore a retroviral etiology for BC in humans (Sarkar, 1980). Data collected over the past five decades has suggested the existence of a human homologue of MMTV. In 1971, Moore and associates reported that 60% of human milk samples from BC patients contain B-type particles indistinguishable from MMTV by electron microscopy, compared to 5% of the general population (Moore et al., 1971). These investigators also reported that 39% of Parsi women of India, an inbred population with a two-fold increased incidence of BC, had B-type particles in their milk (Das et al., 1972; Moore, 1971). Several studies have demonstrated that BC cells, but not cells from normal tissues, also contain reverse transcriptase (RT), an enzyme associated with all retroviruses. Numerous investigators have examined serum and breast milk for the presence of antibodies reactive with MMTV. Most of these studies were performed in the pre-AIDS era, prior to the advent of highly sensitive and specific techniques for detecting anti-retroviral antibodies made necessary for detection of HIV antibodies in donated blood.

Despite the numerous electron microscopic, biochemical and immunological studies on human breast carcinoma tissue, milk, patients' sera, and breast carcinoma cell lines suggesting the existence of a human homologue of MMTV, proof that such an agent exists has remained elusive (Andersson et al., 1996; Ziegler, 1997). Most authors have dismissed the importance of prior studies purporting to show evidence of a human homologue of MMTV because of the presence of numerous human endogenous retroviruses (HERVs) (Larsson et al, 1994; Li et al., 1996; Lower et al., 1996; Meese et al., 1996; Ono, 1986; Patience et al., 1996; Faff et al., 1992). There are about 50,000 HERVs or HERV-related sequences in the human genome, some of which have been shown to have up to 60% homology to MMTV. In this regard, it is important to note that seroreactivity to HERV-K10, to this point the HERV considered to be most closely related to MMTV, cannot account for MMTV-reactive antibodies present in the sera of breast cancer patients and the smaller number of healthy individuals (Vogetseder et al., 1995). Furthermore, we believe that the presence of these MMTV-related sequences is precisely the reason that human homologues of MMTV have not previously been demonstrated conclusively by molecular techniques. The presence of these related, but distinct, sequences could have obscured the detection of more closely related sequences by prior investigators who used less sensitive techniques, such as Southern blotting.

Only recently have sequences with relatively high homology (>90%) to those of MMTV been isolated from human BC tissue (Wang et al., 1995, 1998;). Sequences 95–99% similar to MMTV env were amplified by PCR in 121 (38.5%) of 314 unselected breast cancer tumor samples. It is pertinent to note that the MMTV-like sequences were detected in only 2 (1.8%) of 107 breast specimens from reduction mammoplasties and in 0/80 samples from normal tissues or non-breast tumors. The MMTV-env like RNA was expressed (as determined by RT-PCR) in 66% of DNA PCR positive breast tumors (Wang et al, 1998). A complete 9.9 kb provirus with 94% similarity to MMTV was detected in 2 breast tumors. FISH (fluorescence in situ hybridization) revealed integration at several sites in DNA derived from BC tumors, but not normal breast cells (Wang et al., 1999 ACR mtg. abstracts #2933, 2944). Wang et al. suggested the existence of a human mammary tumor virus (HMTV) that is spread by the exogenous route of infection (horizontal transmission). Attempts by these and other investigators to amplify other regions of MMTV-related viruses, from the genomic DNA or cDNA of subjects who did not have BC, yielded HERV sequences (such as HERV-K10) with only about 60% homology to MMTV. Thus, BC tissues are the only tissues in which sequences that are highly similar to those of MMTV have been heretofore found. Consequently normal breast tissue and other tissues appeared to be negative for the expression of viruses with high homology to MMTV.

MMTV can be Transmitted Horizontally or Vertically

The retrovirus replication cycle is characterized by conversion of the single-stranded RNA viral genome into doubled-stranded proviral DNA by the multiple enzymatic activities of the virion-associated reverse transcriptase (RT). As is the case with other retroviruses, integration of MMTV proviral DNA into the genome of host cells is required for expression of viral proteins and production of infectious progeny. In both infected mouse mammary glands as well as heterologous cells MMTV proviral DNA is integrated into a large number of apparently random sites. Integration of MMTV proviruses containing transcriptionally active LTR near some cellular genes (proto-oncogenes), such as Int, Wnt, and Fgf can result in over-expression of these genes, cellular transformation and clonal expansion of the tumor cells (Varmus, 1985; Shackleford et al., 1993; Jakobovits et al., 1986; Cohen, 1980; Breznik and Cohen, 1982). The long latency of MMTV-induce carcinogenesis is explained in part by the necessity for proviruses to integrate into these particular sites.

Genetic differences among viral strains of MMTV can account in part for the varying incidence of BC in diverse strains of mice. Mice of the C3H strain have a greater than 90% incidence of BC, compared to a <1% incidence of BC in BALB/c mice. BALB/c mice foster-nursed on C3H females have a high incidence of BC which suggested that the tumorigenic MMTV of C3H can be horizontally transmitted in the milk (Bittner, 1936). Conversely, when C3H mice are foster nursed on a BALB/c female the incidence of BC is significantly lower (22–55%), but not as low as low-incidence mouse strains. This latter observation underscores the importance of the horizontally-transmitted milk-born virus in the high incidence strains, but also indicates the substantial differences in tumorigenic potential among endogenous MMTV proviruses. Proviruses of various mice with high and low tumor incidence could be distinguished by differences in solution hybridization kinetics and restriction endonuclease digestion patterns (Cohen et al Cell, 1979; Cohen and Varmus, 1979, 1980; Traina-Dorge and Cohen, 1983; Breznik et al. 1984). Using restriction enzymes that differentiate between hypomethylated and methylated DNA, proviruses of milk-borne MMTV were also shown to be hypomethylated, whereas most endogenous proviruses contain abundant 5-methylcytosine (Cohen, 1980; Breznik and Cohen, 1982; Breznik et al., 1984). Because hypomethylation is associated with increased gene expression, this observation could explain the importance of horizontally-transmined milk-borne MMTV in mouse strains with a high incidence of BC. Specific hypomethylation of an endogenous MMTV provirus was associated with expression of a 1.6 kb transcript of the lactating mammary gland of the BALB/c mouse (Traina-Dorge et al., 1985).

In other studies, endogenous MMTV proviruses have been shown to segregate as stable genetic units during inbreeding and that certain of these endogenous proviruses are transcriptionally active (Cohen et al., Cell, 1979; Cohen and Varmus, 1979, 1980; Traina et al., 1981; Traina-Dorge and Cohen, 1983; Traina-Dorge et al., 1985; Varmus et al., 1978). Recombinant inbred (RI) strains of mice have been used to define MMTV provirus composition and chromosomal locations (Traina et al., 1981; Traina-Dorge and Cohen, 1983). RI strains were developed by crossing mice from two highly inbred lines, randomly mating the F2 generation brothers and sisters and maintaining each as separate lines. Many genetic loci were mapped to specific chromosomes in these strains. By analyzing the segregation patterns of various MMTV proviruses with these genetic markers by restriction endonuclease analysis and Southern blotting, it was possible to determine the chromosomal locations of a number of MMTV proviruses in these strains and to establish that these provirus segregate by the rule of Mendelian inheritance. These and other analyses defined 10 distinct MMTV units (proviruses) in these animals some full length and some truncated. The ratios of inheritance for most of the MMTV proviruses were consistent with simple single-gene inheritance, though three of the MMTV units demonstrated some variance. Most noticeable was the presence of a unit contributed by one parent that was present in 23 of the 26 RI strains analyzed. Specific proviral units were identified that were transcriptionally active and associated with increased tumor production (Traina-Dorge et al., 1985). Importantly, cellular genes were identified that were significantly associated with virus expression showing the involvement of host genetics in disease progression (Traina-Dorge et al., 1985).

Several lines of evidence indicate that the endogenous MMTV proviruses have integrated relatively recently in the germline of various strains of mice (Cohen and Varmus, 1979; Varmus et al., 1978). If MMTV evolved from elements present in a progenitor of Mus musculus (the laboratory mouse), it would be expected that all individual mice would have similar MMTV proviruses. However, both laboratory mice and wild mice trapped at several locations having quite variable numbers and distributions of germline integration sites for their MMTV proviruses (Cohen and Varmus, 1979). The most striking finding among these results were the presence of some wild caught animals that contained no endogenous MMTV proviruses. The most likely interpretation of these results is that the endogenous MMTV proviruses arose by multiple independent integrations into the DNA of germinal cells after speciation of the genus Mus, rather than arising from genetic elements present in the evolutionary progenitors of mice.

SUMMARY OF THE INVENTION

The present invention provides for recombinant DNA molecules derived from one or more mammary tumor viruses which are endogenous retroviruses with homology to the sequences of MMTV. Specifically, the sequences of the instant invention have at least 99% identity with all or a portion of SEQ ID NOs: 2, 3, 4, 5, 6, 7, 8, 21, 23, 25, 27, or 29 or at least 92% identity with SEQ ID NO: 10.

Additionally, the present invention provides for the RNA molecules produced by is transcription of the DNA described above. Furthermore it provides for the polypeptides resulting from the in-frame translation of RNA which has been transcribed from the MTV DNA of the instant invention. According to the present invention, the referenced DNA sequences may be derived from any suitable source, such sources may include, but are not limited to, human, cat, and rhesus macaque.

The present invention also provides for a recombinant DNA plasmid (a vector) which comprises mammary tumor virus (MTV) DNA the sequences of SEQ ID NOs: 2, 3, 4, 5, 6, 7, 8, 10, 21, 23, 25, 27, or 29, or sequences which have at least 99% identity thereto. That is said DNA sequence is incorporated in the vector.

In one embodiment of the present invention the vectors further comprise a heterologous promoter operably linked to the MTV sequence (i.e. joined in the proper reading frame so as to be capable of producing functional MTV RNA and/or protein in vivo and in vitro). In one aspect of this embodiment of the invention the vector, which comprises the MTV DNA, is capable of episomal replication or chromosomal integration in at least one of the following cell types: bacterial cells, yeast cells, insect cells, avian, cells, and mammalian cells (this list of cell types is representative and should not be considered exhaustive). In another aspect, of this embodiment of the invention, the heterologous promoter provides for the expression of the MTV DNA sequence in one or more cell types. Cell types considered useful as part of this aspect of the invention include, but are not limited to the following: bacterial cells, yeast cells, insect cells, avian, cells, and mammalian cells.

According to another embodiment of the instant invention the MTV DNA sequences described above may be used to provide a method of detecting the presence of MTV DNA or RNA in a sample (of biologicalorigin, such as serum, or otherwise).

Another embodiment of the instant invention provides for a method of determining whether a sample contains antibodies which recognize proteins derived from the MTV DNA sequences described above (e.g. polypeptide sequences derived from transcription and translation of SEQ ID NOs: 2, 3, 4, 5, 6, 7, 8, 10, 21, 23, 25, 27, or 29). As a corollary to this aspect, the instant invention also provides for antibodies which specifically detect one or more of the polypeptides of the instant invention.

Another embodiment of the invention provides for diagnostic kits useful for detecting DNA, RNA, or polypeptides, from a mammary tumor virus, in a biological or other type of sample.

Another embodiment of the instant invention provides for methods of attenuating or eliminating the activity of MTV in its host animal. Various aspects of this embodiment provide for pharmaceutical compositions.,comprising substances which disrupt the activity of the MTV reverse transcriptase, protease, or integrase enzymes. Other aspects of this embodiment provide for pharmaceutical compositions capable of eliciting an immune response in a host animal.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1A:
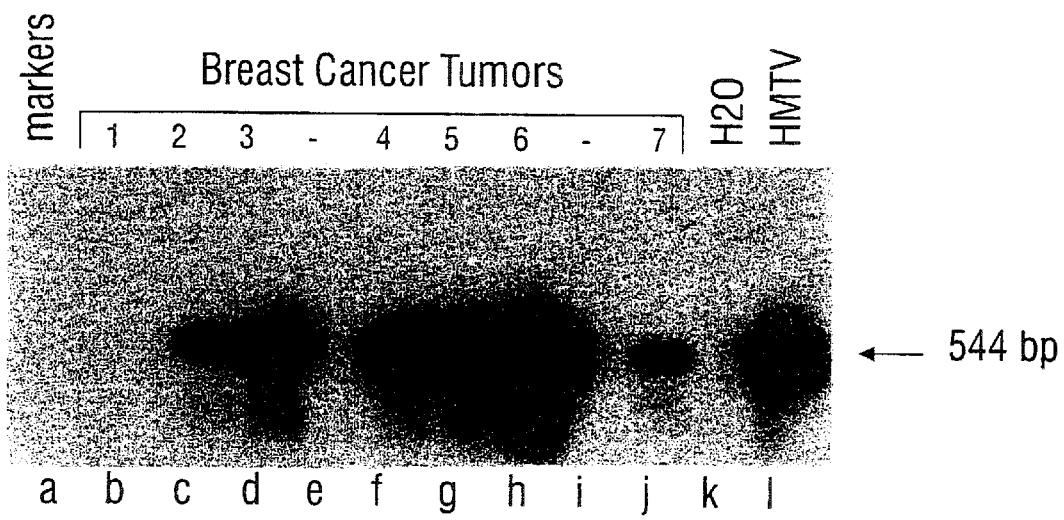
FIG. 1 shows the results of amplification of sequences related to MMTV from human breast cancer tissue Panel A: DNA was extracted from human breast tumors (kindly provided by Michael Press, M.D., USC, Los Angeles or Derrick Beech M.D., TMC/UT Memphis) and PCR was performed using primers specific for the human MMTV env-related gene. PCR products were transferred to nitrocellulose by blotting and MMTV-related products were detected by hybridization to a 1.8 kb MMTV env probe. lane a: nonradioactive markers, not shown; lanes b-d, f-h, j: breast tumor DNA; lanes e and i: no DNA; lane k: water control; lane 1 positive control: MMTV env fragment cloned in pBLUESCRIPT™, DNA vector. Panel B: As a test for the integrity of the DNA from the clinical samples we amplified HERV-3 proviral DNA, a single copy human endogenous retrovirus using PCR conditions developed by Griffiths et at (1997). Ethidium bromide detection (markers are visible in lane a). Same samples as Panel A except lane 1: positive control, HERV3 pol fragment cloned in pBLUESCRIPT™, DNA vector (Stratagene). Visible bands were present in lanes c and g, but do not copy well.

The present invention provides for isolated DNA, RNA, and polypeptides derived from mammary tumor virus (MTV) which is a virus with high sequence homology to mouse mammary tumor virus. The present invention further provides for diagnostic methods of using these macromolecules. Additionally the present invention provides pharmaceutical reagent compositions and diagnostic kits comprising MTV DNA, RNA, and/or polypeptide, which can be used according to the disclosed methods.

Various embodiments of the instant invention provide for MTV nucleic acid corresponding to at least one of the following: DNA sequences with at least 99% identity with one of the following:

a) at least 99% identity with SEQ ID NO: 2, 3, 4, 5, 7, 8, 21, 25, or 27; or b) at least 99% identity with one or more of the following: at least 340 contiguous bases of SEQ ID NO:2, at least 150 contiguous nucleotides of the sequence represented by nucleotides 1–380 of SEQ ID NO:3, at least 140 contiguous nucleotides of the sequence represented by nucleotides 1-400 of SEQ ID NO:4, at least 130 contiguous nucleotides of the sequence represented by nucleotides 1–360 of SEQ ID NO:5, at least 130 contiguous nucleotides of SEQ ID NO:6, at least 140 contiguous nucleotides of the sequence represented by nucleotides 1–380 of SEQ ID NO:7, at least 210 contiguous nucleotides of the sequence represented by nucleotides 20–462 of SEQ ID NO:8, at least 160 contiguous nucleotides of the sequence represented by nucleotides 97-462 of SEQ ID NO:21, at least 170 contiguous nucleotides of SEQ ID NO:23, at least 100 contiguous nucleotides of the sequence represented by nucleotides 337–462 of SEQ ID NO:25, at least 300 contiguous nucleotides of the sequence represented by nucleotides 85-462 of SEQ ID NO:27, or at least 200 contiguous nucleotides of SEQ ID NO:29; or c) at least 92% identity with SEQ ID NO:10.

Preferably the sequences have greater than 99% identity with greater than 200, 250, 300, 350 or 400 nucleotides SEQ ID NO's: 2, 3, 4, 5, 6, 7, 8, 21, 23, 25, 27, or 29. In another preferred embodiment the sequences have greater than 93%, 94%, 95%, 96%, 97%, 98% or 99% identity with SEQ ID NO: 10. Even more preferably these nucleic acids are derived from human, cat, or rhesus macaque MTV's. Most preferably the DNA is identical with all or part of SEQ ID NO's: 2, 3, 4, 5, 6, 7, 8, 10, 21, 23, 25, 27, or 29.

In one aspect of this embodiment of the invention the MTV DNA sequences described above are incorporated in a vector. In various related aspects the invention the MTV sequences are under the transcriptional control of an heterologous promoter. The vectors contemplated as being useful according to the instant invention are capable of expressing the MTV DNA sequences in at least one of the following cell types: insect cells, bacterial cells, avian cells, yeast cells, or mammalian cells. Furthermore the vectors of this aspect of the invention are also capable of episomal replication and/or chromosomal integration in at least one of the cell types listed.

In another aspect of this embodiment the DNA sequences comprise one or more detection moieties. Detection moieties contemplated as being suitable for the instant invention include, but are not limited to fluorescent dyes, and radioactive isotopes of phosphorous, sulfur, oxygen, carbon, or hydrogen.

In yet another aspect of this embodiment of the invention the isolated DNA molecule is suspended or dissolved in a diluent compatible with the invention. Suitable diluents do not interfere with the use of the DNA according to the various embodiments of the instant invention. Diluents useful according to this embodiment of the invention are well known to those skilled in the art. They include but are not limited to buffered aqueous solutions. These may be buffered with any compound compatible with the present invention. Exemplary buffering agents include phosphate buffers and buffers comprising trishydroxyaminomethane (Tris). Such buffered aqueous solutions may further comprise any other compound, such as sodium chloride, which will not interfere with the operation of the instant invention. According to this aspect of the instant invention the MTV DNA may be present in any suitable concentration. Preferably the concentration if from about 0.1 ng/µl to 100 µg/µl.

Other embodiments of the instant invention provide for RNA transcripts and/or polypeptides encoded by the nucleic acids described above. In various aspects of this embodiment these RNA transcripts or polypeptides are encoded by any of the DNA sequences described above. These RNA transcripts and polypeptides are homologues of RNA transcripts and polypeptides encoded by the MMTV env, gag, or pol genes. In one aspect of this embodiment the RNA transcripts are encoded by the DNA sequences described above. Such RNA transcripts have a sequence identical to the disclosed DNA sequence except that the RNA contains uridine instead of thymidine. In another preferred aspect of this embodiment the purified polypeptide corresponds in sequence with all or part of an env, gag, or pro, protein product from a human, cat, or rhesus macaque mammary tumor virus. It is preferred that the peptides be purified polypeptides. In a preferred aspect of the present invention the purified polypeptides are comprised of all or part of the sequence resulting from the in-frame transcription and translation of any of the MTV DNA sequences described above. In an even more preferred aspect of the present invention the polypeptides correspond in sequence to the product of an in-frame translation of SEQ ID NO's: 2, 3, 4, 5, 6, 7, 8, 10, 21, 23, 25, 27, or 29. Most preferably the polypeptide sequences of the instant invention correspond to all or at least 80 amino acids of SEQ ID NO's 12, 13, 14, 15, 16, 17, 18, 20, 22, 24, 26, or 28. The term "derived from MTV DNA" is meant to convey that the RNA or peptide corresponds in sequence to the RNA or peptide produced respectively by the transcription or transcription and in-frame translation of MTV DNA.

By "purified polypeptides" it is meant that the majority (greater than 50%) of the polypeptides in the sample are the MTV polypeptides. Preferably, the MTV polypeptides constitute greater than 70% of the polypeptide in the purified polypeptide sample. More preferably the MTV polypeptide constitutes greater than 90% of the polypeptide in the sample. Even more preferably the MTV polypeptide constitutes greater than 95% of the polypeptide in the sample. Additionally, the term "purified polypeptide" indicates that the sample does not contain substances which interfere with the operation of the instant invention. Purified polypeptides obtained in accordance with the current invention may be from any suitable source which is compatible with the instant invention.

Another embodiment of the instant invention provides for an antibody against an MTV polypeptide as described above. Antibodies according to this aspect of the invention are generated using one or more of the polypeptides of the instant invention as the antigenic agent. Such antibodies may be either monoclonal or polyclonal in nature. Preferably the antibodies are monoclonal. Once the MTV has been provided the antibodies of this aspect of the invention may be prepared according to methods well known to those skilled in the art. For example, polyclonal antibodies are commonly produced by injecting the antigenic agent (in the presence of an immune response enhancing agent such as complete Freunds adjuvant) into an animal such as a sheep, bovine, equine, goat, or rabbit.

Monoclonal antibodies according to this aspect of the present invention can be prepared by hybridoma fusion techniques or by techniques that utilize Epstein Barr Virus (EBV)—immortalization technologies (to produce human mAbs), such as are well known by those of skill in the art, modified as described herein. In the method of the invention, these techniques involve the injection of an immunogen, in this case, purified MTV polypeptide so as to elicit a desired immune response in that animal (i.e., production of antibodies). The experimental animal, (e.g., a mouse) is given repeated injections (boosts) of the same immortalized cell line. In a final step, the animal is given an injection of primary cells of the chosen cell type.

In the illustrative example herein for the production of agonist monoclonal antibodies to megakaryocytic cells, a CMK cell preparation and a CMS cell preparation were used as the first immunogens; however, other immortalized megakaryocytic cells, such as Mo7e or DAMI cells, could have been used. Other monoclonal antibodies analogous to the agonist antibody of the invention BAH-1, which specifically recognizes the C-Mpl receptor, can be generated using if membrane bound c-Mpl receptor protein as the immunogen. To generate agonist monoclonal antibodies against other cell types, other cells of hemopoietic lineage are chosen, e.g., stem cells, B cells or T cells. In the first immunization step stem cells can be represented, e.g., by the immortalized cell line CTS; B cells by the immortalized cell lines ARH-77, SB or Nal-6; and T cells by the immortalized cell lines Jurkat or H9.

After a sufficient time, the animal is sacrificed and somatic antibody-producing cells may be derived from the lymph nodes, spleens and peripheral blood of primed animals. Spleen cells are preferred. Mouse lymphocytes give a higher percentage of stable fusions with the mouse myelomas described below. The use of rat, rabbit, frog, sheep and other mammalian somatic cells is also possible. The spleen cell chromosomes encoding desired immunoglobulins are immortalized by fusing the spleen cells with myeloma cells, generally in the presence of a fusing agent such as polyethylene glycol (PEG). Any of a number of myeloma cell lines may be used as a fusion partner according to standard techniques; for example, the P3-NS1/1-Ag4-1, P3-x63-Ag8.653 or Sp2/0-Ag14 myeloma lines. These myeloma lines are available from the American Type Culture Collection (ATCC), 10801 University Boulevard, Manassas, Va. 20110-2209.

The resulting cells, which include the desired hybridomas, are then grown in a selective medium, such as HAT medium, in which unfused parental myeloma or lymphocyte cells eventually die. Only the hybridoma cells survive and can be grown under limiting dilution conditions to obtain isolated clones. The supernatants of the hybridomas are screened for the presence of antibody of the desired specificity, e.g., by immunoassay techniques such as those described herein, using the antigen that has been used for immunization. Positive clones can then be subcloned under limiting dilution conditions and the monoclonal antibody produced can be isolated. Various conventional methods exist for isolation and purification of the monoclonal antibodies so as to free them from other proteins and other contaminants. Commonly used methods for purifying monoclonal antibodies include ammonium sulfate precipitation, ion exchange chromatography, and affinity chromatography. Hybridomas produced according to these methods can be propagated in vitro or in vivo (in ascites fluid) using techniques known in the art (see, generally, Harlow et al., Antibodies. A Laboratory Manual, Cold Spring Harbor Laboratory, pp. 1–726, 1988).

Other embodiments of the instant invention provide methods for detecting DNA, RNA, and/or proteins from MTV in biological and/or other types of samples.

One aspect of this embodiment of the invention provides a method for the detection of MTV DNA in a sample which comprises the following steps:

i) obtaining an sample suspected of containing one or more of the MTV DNA sequences described above;

ii) carrying out a polymerase chain reaction (PCR) to amplify a DNA sequence as defined in step i); and, iii) determining the sequence of, or otherwise characterizing, the amplicons (the PCR amplified DNA) produced in step ii) to determine whether or not the DNA sequence as defined in step i) is present in the sample.

Another aspect of this embodiment provides a method for the detection of MTV RNA in a sample which comprises the following steps:

i) obtaining an sample suspected of containing RNA which encoded by one or more of the MTV DNA sequences described above;

iii) carrying out an RNAse protection assay (RPA); and, iii) analyzing the RPA results to determine whether RNA as defined in step i) is present in the sample and optionally quantitating said RNA.

It will be recognized by those of ordinary skill that the selection of the parameters necessary for optimizing the steps of these methods are well within the abilities of the ordinarily skilled artisan. These parameters, for example PCR conditions (e.g. selection of annealing temperature, extension times, and primers) and DNA sequencing method, are routinely determined in labs where such molecular biological techniques are employed.

Another aspect of this embodiment of the invention provides for a method for analyzing a ample in order to determine whether the sample contains antibodies which recognize MTV polypeptides. This method comprises the steps of:

i) obtaining a sample suspected of containing antibodies specific for mammary tumor viral antibodies;

ii) obtaining at least one purified MTV polypeptide;

iii) performing western immunoblot analysis using the sample of step i) and the polypeptide of step ii); and, iv) analyzing the results of step iii) to determine whether or not antibodies which specifically interact with the peptide of step ii) are present in the sample.

Another aspect of this embodiment of the invention provides for a method for analyzing a cell culture or a tissue sample by one or more immunohistological methods in order to determine whether the sample contains MTV proteins. This method comprises the steps of:

i) obtaining a sample suspected of containing mammary tumor viral proteins;

ii) preparing the sample of step i) for immunochemical analysis;

iii) incubating the sample of step ii) with one or a combination of two or more monoclonal or polyclonal antibodies specific for MTV polypeptides encoded by one or more of the MTV DNA sequences described above, wherein the said antibodies optionally have a moiety which allows for their specific detection;

iv) washing the samples to remove antibody which is not specifically bound;

v) processing the samples as appropriate for the selected detection method; and, vi) analyzing the results of step v.) to determine whether or not MTV proteins are present in the sample.

It is envisioned that the immunochemical analysis may include, but is not limited to analysis by western blotting or enzyme-linked immunosorbant assay. It will be recognized that the selection of the parameters necessary for optimizing the performance of these methods are within the abilities of the ordinarily skilled artisan. Analysis may be performed using either direct immunochemistry (if the antibodies have been labeled with a detectable moiety) or by indirect immunochemistry.

Other embodiments of the current invention provide for pharmaceutical compositions comprising MTV DNA, RNA and/or proteins described supra. These compositions may further comprise a pharmaceutically acceptable excipient, carrier, or diluent and do not contain any biologically harmful substances. The pharmaceutical compositions of the present invention may be formulated by one having ordinary skill in the art. Suitable pharmaceutical formulations are described in Remington's Pharmaceutical Sciences which is a standard reference text in the field which is here in incorporated by reference.

The pharmaceutical compositions may further comprise coloring or stabilizing agents, osmotic agents, antibacterial agents, or any other substances as long as such substances do not interfere with the function of the composition. The pharmaceutical compositions of the invention, can, for example, be formulated as a solution, suspension, or emulsion in association with a pharmaceutically acceptable parenteral vehicle. Examples of such vehicles are water, saline, Ringer's solution, dextrose solution, and 5% human albumen. Liposomes may also be used. The vehicle may contain additives that maintain isotonicity (e.g., sodium chloride or mannitol) and chemical stability (e.g., buffers and preservatives). It should be appreciated that endotoxin contamination should be kept at a safe level, for example, less than 0.5 ng/mg protein. Moreover, for human administration, preparations should meet sterility, pyrogenicity, general safety and purity standards as required by the United States Food and Drug Administration Office of Biological Standards. The formulations may be sterilized by commonly used techniques such as filtration.

The phrase "pharmaceutically acceptable" refers to substances and compositions which do not produce an adverse, allergic, or otherwise untoward reaction when administered to an animal, or a human, as appropriate. A substance which caused produced any of these adverse effects would be classified as "biologically harmful" within the scope of the present invention. Pharmaceutically acceptable substances and compositions include, but are not limited to solvents, dispersion media, coatings, antibacterial and antifungal agents, isotonic and absorption delaying agents. Except where incompatible with the invention the use of any conventional ingredient is contemplated. Furthermore, supplementary active ingredients which serve some other pharmacologically expedient purpose can also be incorporated into the instant compositions.

The methods and compositions described above are contemplated to be of great benefit in helping to determine whether or not MTV or MTV viral components are present in a person's tissues. This knowledge is would be of aid in predicting a patient's susceptibility to cancer etiologically derived from MTV. The methods provide a means for determining a patients viral load (the amount of virus present in the person's tissues). In this respect it is envisioned that tremendous benefit would be achieved by adapting the methods herein described to the widespread screening of the general population, and in particular to all mature human females.

Other compositions contemplated as part of various embodiments of the instant invention provide a means for stabilizing or reducing the amount of virus present in a human or other animal.

The various methods described above are readily adaptable to preparing diagnostic kits for detecting the presence of MTV DNA, RNA, and/or polypeptides. Consequently, for the clinical practice of the invention, yet other embodiments of the instant invention, which provide for diagnostic kits, are contemplated. Such kits are useful for the qualitative and quantitative analysis of a sample in order to detect, and perhaps determine the quantity of, MTV DNA, RNA, and/or polypeptide present therein. In one aspect of this embodiment of the invention the kit includes, as part of its components, one or more recombinant DNA molecules comprising one or more of the MTV DNA sequences described above. Also according to this aspect of the invention the kit may comprise, in addition to (or in alternative to) the recombinant MTV DNA, one or more synthetic oligonucleotide primer pairs useful for the PCR amplification of these MTV DNA sequences.

Another aspect of this embodiment of the invention provides for a kit for detecting antibodies which specifically recognize mammary tumor virus proteins. As part of its components this kit includes a reagent comprising one or more polypeptides encoded by the MTV DNA sequences described above.

Also contemplated are kits useful for detecting the presence of MTV proteins by immunocytochemistry which comprise one or more antibodies (either monoclonal or polyclonal) which are specific for at least one MTV polypeptide. Optionally, these antibodies may be modified so as to comprise a detection moiety (e.g., a fluorescent die or a radioactive isotope, such as $^{35}S$).

Kits according to these embodiments of the invention may comprise packages, each containing one or more of the various reagents (typically in concentrated form) which are required to perform the respective diagnostic tests. The kits according to these embodiments of the invention are contemplated to be useful for detecting and/or quantifying MTV DNA. RNA, and/or protein in biological (or other types of) samples. Such samples may be selected from, but are not limited to the following: blood plasma or serum, whole blood, urine, sputum, colonic effluent, cerebrospinal fluid, lymphatic fluid, bone marrow, tissue samples (such as from a surgical biopsy), or any other sample suspected of containing these biological molecules.

The kits also may further include one or more fiduciary results. As used herein a "fiduciary result" refers to a reference standard against which a test outcome is compared to gauge the results in terms of quality and/or quantity. A "fiduciary series" is a plurality of such references that represent points along a qualitative or a quantitative scale. Preferable in this regard, are kits that include a fiduciary series for interpreting results. The fiduciary may be in the form of one or more photographs or may be depicted in other ways, including written descriptions.

Thus fiduciaries may be developed as part of the kits, in accordance with this aspect of the invention, to guide interpretation of results. In this regard, a RNA or polypeptide concentration from a biological sample may be characterized in accordance with the foregoing. Sample may be taken from representative cross-section of patients at various stages of disease (including asymptomatic or essentially disease free) to prepare a fiduciary series. Characterization in this regard may benefit from hindsight, by following the actual course of neoplastic progression in patients as they undergo diagnosis, treatment, and follow up thereafter. The determination of viral load (as determined by the abundance of MTV DNA, RNA, or polypeptide), as set out above, for a variety of patients of known breast cancer status and eventual outcome, and the subsequent correlation of these values is of incalculable prognostic value. This will help provide the patient with a more accurate prognosis, and it will also aid the patient and oncologist in determining the best course of therapeutic treatment, when such treatment is necessary.

Another embodiment of the instant invention provides for a composition which induces an immunological response against MTV in an animal. A specifically contemplated aspect of this invention is a composition which induces an immunological response to human mammary tumor viral protein in humans (see Example 7). It is expected that such induced immunity may prevent breast cancer in individuals that carry endogenous MTV, by blocking the spread of the virus to hormonally sensitive tissues.

Methods for producing an immune response to viral DNA and/or RNA in animals are also known, see for example U.S. Pat. Nos. 5,990,091 and 6,004,799 which are herein incorporated by reference. Thus compositions which elicit an immune response to MTV DNA and/or RNA are also contemplated as aspect of this embodiment of the invention.

Other embodiments provide for therapeutic compositions which decrease the activity and presence of human mammary tumor virus. A common feature of all retroviruses is the presence of three enzymes involved in various stages of the viral replication cycle, the reverse transcriptase (RT), protease (PR), and integrase (IN). Various pharmaceuticals have been developed which target the RT and PR of human immunodeficiency virus (HIV), a retrovirus distantly related to MTV. Furthermore, chemicals which selectively inhibit HIV IN have been identified and prototype drugs targeting this enzyme are under development (Hong et al., 1998; Mathe, 1999; Robinson, 1998; Singh et al., 2000). According to one aspect of the instant invention a pharmaceutical composition comprising one or a mixture of two or more retroviral inhibitors in an amount effective to inhibit the activity or the spread of MTV's of the instant invention is provided.

Identification of the drug or drugs for use in the pharmaceutical compositions of this embodiment can be made using techniques known to those skilled in the art. For examples of protease and reverse transcriptase inhibitors and methods of determining the efficacy of such drugs as retroviral inhibitors see U.S. Pat. Nos. 5,858,738, 6,017,928, and 6,046,228, which are herein incorporated by reference. The various compositions of this embodiment of the invention may comprise, for example, currently known HIV integrase, protease, or reverse transcriptase inhibitors; alternatively, such inhibitors can be modified so as to increase their specificity for MTV's. Likewise, other classes of HIV inhibitors, such as peptides which are analogs of the transmembrane glycoprotein, can serve as pro-drugs to develop specific drugs which decrease activity and presence of MTV in humans and other species. These compositions are contemplated as being useful to inhibit the activity and spread of MTV in humans and other species which carry these viruses as endogenous genetic elements. Such drugs could be used to treat breast cancer patients afflicted with MTV and would be expected to ameliorate the severity and to reduce the recurrence of disease. In addition, such drugs could be used prophylactically to prevent the occurrence of individuals at high risk for developing the disease.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain same or similar result without departing from the spirit and scope of the invention.

Example 1

MMTV-related Sequences in Humans

Figure 1B:
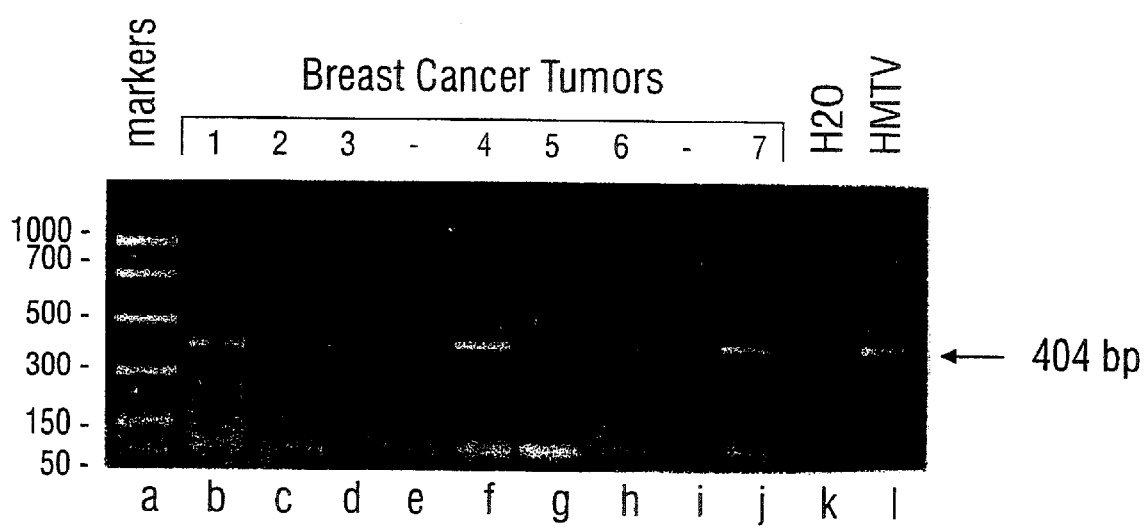
Figure 2A:
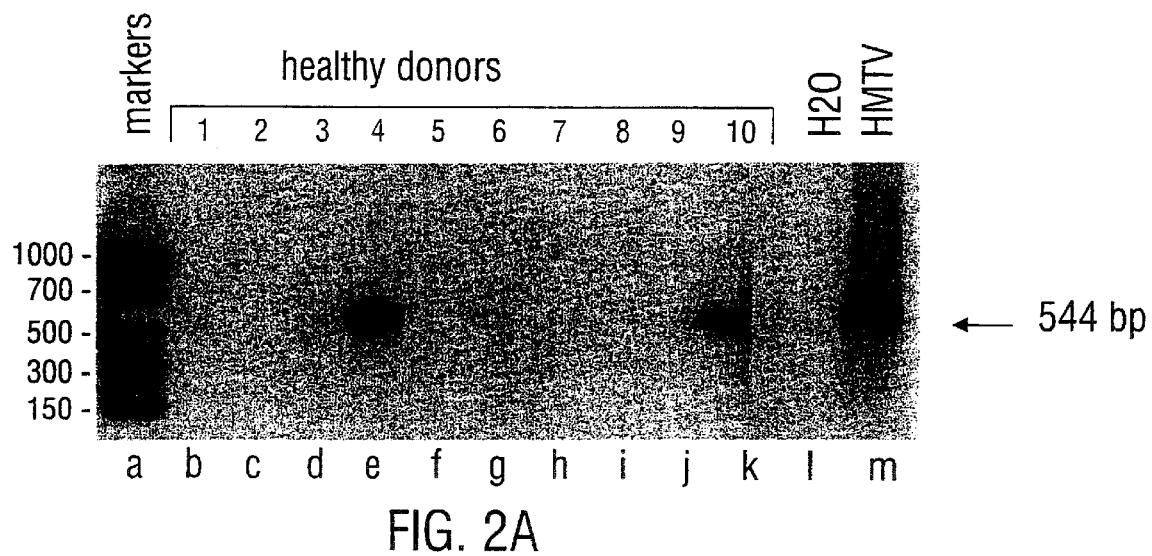
FIG. 2 shows an example of the amplification of sequences related to MMTV from the blood of healthy controls. Panel A DNA was extracted from whole blood of healthy control subjects and PCR was performed using primers specific for the human MMTV env-related gene and PCR products were detected by Southern hybridization. lane a: markers; lanes b-k: DNA from whole blood of healthy controls; lane 1: water control; lane m positive control: MMTV env fragment in pBLUESCRIPT™, DNA vector (Stratagene). Panel B: PCR amplification of HERV-3. Ethidium bromide detection (markers are visible in lane a). Same samples as Panel A except lane m: positive control, HERV3 pol fragment in pBLUESCRIPT™, DNA vector.
Figure 2B:
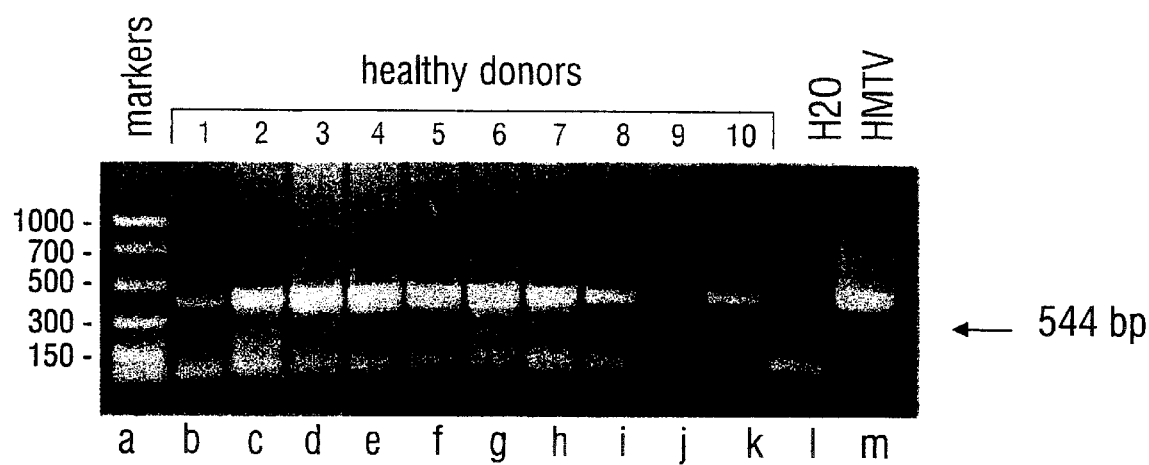

Sequences which are highly similar (>95%) to the MMTV env gene were amplified by PCR from human DNA samples, including subsets of both BC (breast cancer) tissue and non-BC tissues. The MMTV-related sequences were found by PCR and a sensitive blotting technique not only in breast tumors (see FIG. 1), but also in the blood of a subset of healthy controls (see FIG. 2), and systemic lupus erythematosus (SLE) patients without breast cancer. Our results differ from those of Wang and coworkers (1995) who, with few exceptions, were able to detect MMTV-like sequences only in breast tumors. The sequences from human DNA were distinct from the MMTV sequences used as controls in these PCR reactions indicating that our results are not simply due to contamination. A ribonuclease protection assay was used to confirm these results using a non-PCR based technique to determine that the majority of the PCR positive BC tissues, but none of the PCR negative tissues, expressed this sequence at the mRNA level. Many of the products from these PCR reactions have been sequenced. Analysis of these sequences provides further strong evidence that PCR contamination is an unlikely explanation for the observed results. MMTV env-like sequences from different individuals derived in the same PCR run were distinct from each other. This result indicates the lack of an ubiquitous PCR contaminant that would have produced a more consistent sequence that should have been identical (or nearly so) in the various reaction tubes. Furthermore DNA of individual subjects produced internally consistent MMTV env-like sequences from PCR run to PCR run. The variations within the MMTV-related sequences from a given patient may represent a low number of Taq errors, but are also suggestive of variations expected of a replicating retrovirus (reverse trascriptase errors).

Example 2

RNase Protection Assay Determination of MTV RNA Levels

Figure 3:
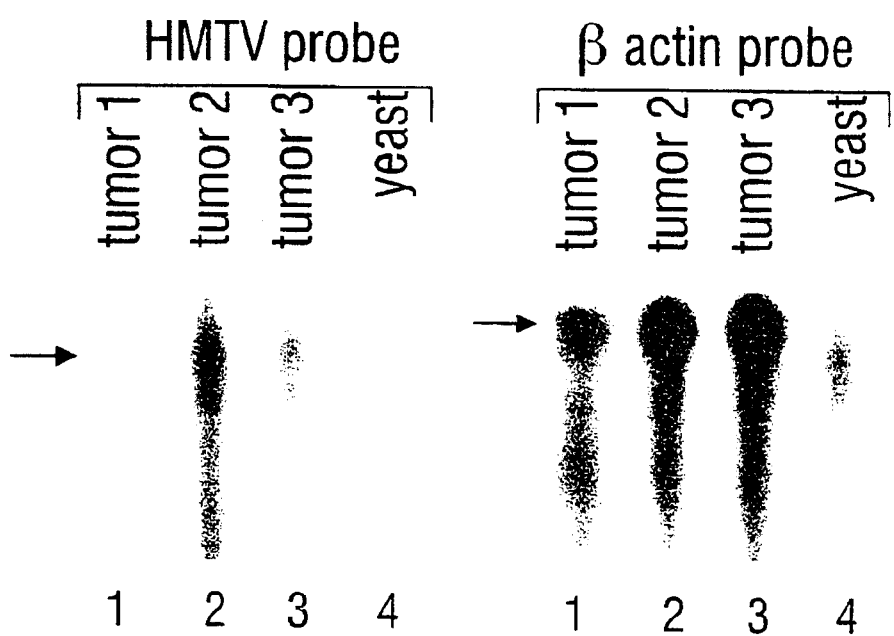
FIG. 3 shows an example of the detection of HMTV mRNA by ribonuclease protection assay. RNA was extracted from three HMTV PCR positive breast cancer tumors or from yeast 20 cells and hybridized to either 189 base probe specific for HMTV or a 245 base probe for β-actin. Samples were then digested with RNAse A/T1. The fragments of the labeled probes protected by hybridized RNA were visualized and analyzed following separation on a denaturing polyacrylamide gel. Two of the three tumor samples gave protected fragments of the expected size with the HMTV probe (arrow) (lanes 1–3), whereas all three tumor RNAs gave protected fragments with the M-actin probe (lanes 5–7). As expected neither probe was specifically protected by yeast RNA (lanes 4, 8).

Ribonuclease protection assay (RPA) is a quantitative assay which is frequently used by those of ordinary skill in the art to determine the levels of specific RNA species without PCR amplification. Briefly, it is performed as follows for the transcripts of the present invention: a probe of uniform length is synthesized by in vitro transcription of a cloned template and labeled to high specific activity. $[^{35}S]$-labeled riboprobes were prepared from plasmids containing the cloned MTV fragments in the 150 to 400 bp size range. The probe was then hybridized to test RNA, and RNA fragments that remain unhybridized are not protected from digestion by RNAse A/T1. The fragments of the labeled riboprobe protected by hybridized RNA were visualized and analyzed following separation on a denaturing polyacrylamide gel. Levels of MTV-related mRNA are compared in each sample to levels of mRNA produced by the β-actin gene, a "housekeeping" gene to ensure integrity of the RNA sample (i.e., that the RNA has not been degraded). RPA detected RNA in 2 out of 3 PCR positive breast tumors (see FIG. 3). RPA is 10–15 times more sensitive than "northern" analysis for detection of rare messenger RNA. RPA analysis is performed directly on total RNA, without any prior manipulation, which can introduce errors in the quantitative analysis.

Example 3

RT-PCR determination of MTV RNA Levels

MTV mRNAs may also be detected using real time RT-PCR (reverse transcriptase linked polymerase chain reaction). For example the I-Cycler (Biorad), with a fluoroscopic detection facility is capable of determining the real time kinetics of the PCR amplification product by quantifying the PCR product in the log-linear phase of the PCR reaction. Using this method, a real-time thermocycler can reliably compare miniscule amounts of known nucleotide template in a reproducible fashion.

Example 4

Detection of Anti-MTV Antibodies in Blood by Western Blot Analysis

The INSECTSELECT™, insect cell protein expression system (Invitrogen) which allows stable production of recombinant proteins in insect cells in a manner similar to well-characterized baculovirus expression systems may be used to generate recombinant MTV proteins. This is a virus-free system which allows creation of stable cell lines that continuously produce high-quality protein. Stable cell lines generated in about 9 days may be used for continuous, long-term production of recombinant proteins. The INSECTSELECT™, insect cell protein expression system expression system is based on a plasmid vector which carries an antibiotic resistance gene for selecting stably expressing insect cell lines. This expression vector uses the immediate early promoter, OpIE2, from the Douglas Fir Tussoc moth OpMNPV baculovirus for gene expression. OpIE2 is a strong transcriptional promoter in lepidopterin (Sf9, 5121, HIGH FIVE™, insect cells (Invitrogen)) as well as mosquito and dipterin cell lines. The expression vector pIZ/V5-His (Invitrogen) has a multiple cloning site and several features that simplify production and analysis of recombinant proteins in insect cells. It includes a Zeocin-resistance gene that allows for rapid selection of stably transfected cells, a C-terminal tag encoding the V5 epitope, and a C-terminal polyhistidine (6×His) sequence. These latter features facilitate rapid protein detection with anti-V5 antibodies (Invitrogen) and protein purification with resins that bind the polyhistidine. Alternative eukaryotic expression systems for MMTV related proteins are an in vitro rabbit reticulocyte lysate system (Promega) with in vitro transcribed and capped mRNA or the Sindbis virus Expression system Invitrogen).

MMTV-related genes may also be cloned into a pGEX vector (Pharmacia) and expressed in bacteria to make recombinant fusion protein with glutathione S-transferase (GST) protein for immunoblot studies. This system has several advantages compared to other methodologies of protein expression, not the least of which is the ease of production, isolation, and purification of the recombinant protein. Fusion proteins generated with the GST protein typically remain soluble permitting the recovery from cell lysates. Denaturing conditions are not required during purification and therefore the antigenic and enzyme properties of the protein are often maintained. Moreover, the GST fusion protein may be efficiently and rapidly purified by immobilizing the GST on glutathione coated beads or columns and eluted with reduced glutathione.

To perform a western innunoblot, MTV proteins are dissolved in lysis buffer (0.25 M Tris Base, pH 6.8, containing 4% sodium dodecyl sulfate, 10% dithiothreitol, 20% glycerol, and 0.01% w/v bromophenol blue), heated to 100° C. for min and subjected to sodium dodecyl sulfate-polyacrylamide gel electrophoresis (SDS-PAGE) on a 10% polyacrylamide gel. These proteins may then be transferred electrophoreucally to a nitrocellulose membrane PROTRAN™, nitrocellulose membrane; Schleicher & Schuell) in Tris-glycine (pH 9.3) buffer with 20% methanol. The blots may be incubated overnight in blocking buffer (0.02 M Tris, 0.1 M NaCl, heat inactivated goat serum, 0.01% timerosal, and 5% nonfat dry milk) with serum or plasma from the human or animal being tested (1:100 dilution or optimal dilution). Incubation with secondary antibodies, biotinylated anti-human (or other species) IgG goat antibodies diluted 1:500 or 1:1,000 in blocking buffer, and with avidin-horseradish peroxidase may be performed at room temperature for 2 hours. The immunoblots may be developed with 7.8 mM 4-chloro-1-napthol and 0.03% hydrogen peroxide. Bands corresponding to MTV proteins are quantitated by scanning and processed with image analysis software (NIH Image).

Example 5

Detection of Anti-MTV Antibodies by Enzyme Linked Immunoassay

Altibodies which specifically bind to MTV protein(s) may be detected using an enzyme-linked immunoassay with MTV protein or proteins as the target for the antibodies. In this technique MTV proteins produced in an expression system, such as the baculovirus/insect cell clutter system or purified from virus preparations may be bound to the bottom of wells in a multiwell plastic microtiter plate. Serum or plasma from humans or other species is diluted to an empirically determined optimum dilution and incubated from 1 hour to overnight at about 25° C. (room temperature). The wells are then washed three times in a saline solution containing TWEEN® 20 (Aldrich) or NP-40 (currently available as IGEPAL™ CA-630, Sigma) detergents using an automated plate washer. Antibodies bound to the MTV proteins may then be detected by reacting the wells sequentially with buffers containing biotinylated goat anti-hunan immunoglobulin, followed by avidin coupled to horseradish peroxidase, and finally 3,3', 5,5'-tetramethylbenzidine a substrate for horseradish peroxidase which produces a colored reaction product. Between each step the well is typically washed three times in a saline solution containing TWEEN® 20 or NP-40 detergents using an automated plate washer. The colored reaction produced in each well is quantitated using a spectrophotomreter plate reader. The amount of colored reaction product is proportional to the amount of antibodies to MTV present in the original sample.

Example 6

Detection of MTV Retroviral Proteins In Situ Using Immunohistochemistry

MTV retroviral proteins may be detected in tissue samples by immunohistochemical assays. In this technique MTV proteins produced in an expression system, such as the baculovirus/insect cell clutter system or purified from virus preparations may be used to generate monoclonal or polyclonal antibodies by methods well known to those skilled in the art. These antibodies may then be labeled with a detection moiety such as biotin, fluorescein, horseradish peroxidase or other labels used for this purpose. The labeled antibody preparations are then diluted to an empirically determined optimum dilution and incubated with fixed or frozen thin sections or cell preparations from samples to be tested for the presence of MTV proteins. The samples are processed, as dictated by the type of label used, and the binding of the antibody to MTV retroviral proteins may be detected by microscopy, autoradiography, flow cytometry, etc., again, as dictated by the identity of the labeling moiety.

Example 7

Preparation of a Pharmaceutical Composition Capable of Eliciting an Immunological Response, Against Human Mammary Tumor Virus, in Humans A pharmaceutical composition to be used to induce an immunological response an in humans or animals to MTV protein may be developed as follows. MTV proteins produced in an expression system, such as the baculovirus/insect cell culture system described above or purified from virus preparations may be extensively purified using column chromatography and/or any other methodologies commonly employed by skilled artisans. The purified MTV proteins may then be mixed or emulsified with a suitable adjuvant preparation (currently alum is the only adjuvant approved for use in humans) to produce a vaccine. This immunogenic composition may then be injected subcutaneously or intradermally into the target animal.

All of the composition and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Andersson, M. L., Medstrand, P., Yin, H., and Blomberg, J. (1996). Differential expression of human endogenous retroviral sequences similar to mouse mammary tumor virus in normal peripheral blood mononuclear cells. *AIDS Res Hum Retroviruses* 12, 833–40.

Armstrong, K., Eisen, A., and Weber, B. (2000). Assessing the Risk of Breast Cancer. *NEJM* 342, 564–571.

Bittner, J. (1936). Some possible effects of nursing on the mammary gland tumor incidence in mice., *Science* 84, 162–166, 1936.

Breznik, T. and Cohen, J. C. (1982). Altered methylation of endogenous viral promoter sequences during mammary carcinogenesis. *Nature* 295, 255–257.

Breznik, T. Traina-Dorge V., Gama-Sosa M., Gehrke C. W., Ehrlich M., Medina D., Butel, J. S., Cohen, J. C. (1984). Mouse mammary tumor virus DNA methylation: tissue-specific variation, *Virology*. 136, 69–77.

Coffin, J. M. (1992). Superantigens and endogenous retroviruses: a confluence of puzzles, *Science* 255, 411–3.

Cohen, J. C. (1980). Methylation of milk-borne and genetically transmitted mouse mammary tumor virus proviral DNA, *Cell*. 19, 653–62., 1980.

Cohen, J. C. and Varmus, H. E. (1979). Endogenous mammary tumor virus DNA varies among wild mice and segregates during inbreeding. *Nature* 278, 418–423.

Cohen, J. C. and Varmus, H. E. (1980). Proviruses of mouse mammary tumor virus in normal and neoplastic tissues from GR and C3Hf mouse strains. *J Virology* 35, 298–305.

Cohen, J. C., Majors, J. E., and Varmus, H. E. (1979). Organization of mouse mammary tumor virus-specific DNA endogenous to BALB/c mice. *J Virology* 32, 483–496.

Cohen, J. C., Shank, P. R., Morris, V. L., Cardiff, R., and Varmus, H. E. (1979). Integration of the DNA of mouse mammary tumor virus in virus-infected normal and neoplastic tissue of the mouse. *Cell* 16, 333–345.

Cohen, J. C., Traina, V. L., Breznik, T., Gardner, M. (1982). Development of an MMTV negative strain: a new system for the study of mammary carcinogenesis. *J Virology* 44, 882–885.

Das, M. R., Vaidya, A. B., Sirsat, S. M., and Moore, (1972). D. H. Polymerase and RNA studies on milk virions from women of the Parsi community, *J Natl Cancer Inst.* 48, 1191–6.

Faff, O., Murray, A. B., Schmidt, J., Leib-Mosch, C., Erfle, V., and Hehlmann, R. (1992). Retrovirus-like particles from the human T47D cell line are related to mouse mammary tumour virus and are of human endogenous origin *J Gen Virol.* 73, 1087–97.

Gayther, S. A., Pharoah P. D., and Ponder B. A. (1998). The genetics of inherited breast cancer. *J Mammary Gland Biol Neoplasia* 3, :365–76.

Golovkina, T. V., Dudley, J. P., Jaffe, A. B., and Ross, S. R. (1995). Mouse mammary tumor viruses with functional superantigen genes are selected during in vivo infection, *Proc Natl Acad Sci USA* 92; 4828–32.

Hong, H., Meamati, N., Winslow, H. E., Christensen, J. L., Orr, A., Pommier, Y., and Milne, G. W. (1998) Identification of HIV-1 integrase inhibitors based on a four-point pharmacophor. *Antivir. Chem. Chemother.* 9, 461–72.

Jakobovits, A., Shackleford, G. M., Varmus, H. E., and Martin, G. R. (1986). Two proto-oncogenes implicated in mammary carcinogenesis, int-1 and int-2, are independently regulated during mouse development. *Proc Natl Acad Sci USA* 83, 7806–10.

Ktajewski, J., Mason, J. O., and Varmus, H. E. (1992). Interaction of Wnt-1 proteins with the binding protein BiP, *Mol Cell Biol* 12, 784–90.

Kitamura, Y., Ayukawa, T., Ishikawa, T., Kanda, T., and Yoshiike, K. (1996). Human endogenous retrovirus K10 encodes a functional integrase. *J Virol.* 70, 3302–6.

Larsson, E., Andersson, A. C., and Nilsson, B. O. (1994). Expression of an endogenous retrovirus (ERV3 HERV-R) in human reproductive and embryonic tissues—evidence for a function for envelope gene products. *Ups JMed Sci.* 99, 113–20.

Li, J. M., Fan, W. S., Horsfall, A. C., Anderson, A. C., Rigby, S., Larsson, E., and Venables, P. J. (1996). The expression of human endogenous retrovirus-3 in fetal cardiac tissue and antibodies in congenital heart block *Clin Exp Immunol.* 104, 388–93.

Lower, R., Lower, J., and Kurth, R. (1996). The viruses in all of us: characteristics and biological significance of human endogenous retrovirus sequences, *Proc Natl Acad Sci USA* 93, 5177–84.

Luther, S. A. and Acha-Orbea, H. (1996). Immune response to mouse mammary tumour virus, *Curr Opin Immunol.* 8, 498–502.

Mathe, G. (1999) Why have ten or so nontoxic, retrovirus integrase inhibitors not been made available for AIDS treatment? A ten-year experience [correction of experiment] must liberate them, *Biomed Pharmacother.* 53, 484–86.

May, F. E. and Westley, B. R. (1986). Structure of a human retroviral sequence related to mouse mammary tumor virus, *J Virol.* 60, 743–9.

Meese, E., Gottert, E., Zang, K. D., Sauter, M., Schommer, S., and Mueller-Lantzsch, N. (1996). Human endogenous retroviral element K10 (HERV-K10): chromosomal localization by somatic hybrid mapping and fluorescence in situ hybridization *Cytogenet Cell Genet.* 72, 40–2.

Moore, D. H. (1971). Evidence for a human breast cancer virus, *Indian J Cancer* 8, 80–3.

Moore, D. H., Charney, J., Kramarsky, B., Lasfargues, E. Y., Sarkar, N. H., Brennan, M. J., Burrows, J. H., Sirsat, S. M., Paymaster, J. C., and Vaidya, A. B. (1971). Search for a human breast cancer virus, *Nature* 229, 611.

Nusse, R. (1991). Insertional mutagenesis in mouse mammary tumorigenesis, *Curr Top Microbiol Immunol.* 171, 43–65.

Nusse, R., Brown, A., Papkoff, J., Scambler, P., Shackleford, G., McMahon, A., Moon, R., and Varmus, H. (1991). A new nomenclature for int-1 and related genes: the Wnt gene family *Cell* 64, 231.

Nusse, R., van Ooyen, A., Rijsewijk, F., van Lohuizen, M., Schuuring, E., and van't Veer, L. (1985). Retroviral insertional mutagenesis in murine mammary cancer, *Proc R Soc Lond B Biol Sci.* 226, 3–13.

Ono, M. (1986). Molecular cloning and long terminal repeat sequences of human endogenous retrovirus genes related to types A and B retrovirus genes, *J Virol.* 58, 937–44.

Patience, C., Simpson, G. R., Colletta, A. A., Welch, H. M., Weiss, R. A., and Boyd, M. T. (1996). Human endogenous retrovirus expression and reverse transcriptase activity in the T47D mammary carcinoma cell line *J Virol.* 70, 2654–7.

Remington's Pharmaceutical Sciences, Alfonso R. Gennaro Ed., $16^{th}$ Edition, 1980.

Robinson, W.E. Jr. (1998) L-chicoric acid, an inhibitor of human immunodeficiency virus type 1 (HIV-1) integrase, improvews on the in vitro anti-HIV-1 effect of Zidovudine plus a protease inhibitor (AG1350), *Aniviral Res.* 39, 101–11.

Sambrook et al., "Molecular Cloning: A Laboratory Manual," Cold Spring Harbor Laboratory, Cold Spring Harbor, N.Y., 1989.

Sarkar, N. H. (1980). B-type virus and human breast cancer. In: G. Giraldo and E. Beth (eds.), The role of viruses in human cancer, pp. 207–235. New York: Elsevier.

Shackleford, G. M. and Varmus, H. E. (1987). Expression of the proto-oncogene int-1 is restricted to postmeiotic male germ cells and the neural tube of mid-gestational embryos, *Cell* 50, 89–95.

Shackleford, G. M., MacArthur, C. A., Kwan, H. C., and Varmus, H. E. (1993). Mouse mammary tumor virus infection accelerates mammary carcinogenesis in Wnt-1 transgenic mice by insertional activation of int-2/Fgf-3 and hst/Fgf4. *Proc Natl Acad Sci USA* 90, 740–4.

Sing, S. B., Felock, P., and Hazuda, D. J. (2000) Chemical and enzymatic modifications of integric acid and HIV-1 integrase inhibitory activity, *Bioorg. Med Chem. Lett.* 10, 235–38.

Traina, V. L., Taylor, B. A., and Cohen, J. C. (1981). Genetic mapping of endogenous mouse mammary tumor viruses: locus characterization, segregation, and chromosomal distribution, *J Virology* 40, 735–44.

Traina-Dorge, V. and Cohen, J. C. (1983). Molecular genetics of mouse mammary tumor virus, *Curr Top Microbiol Immunol* 106, 35–56.

Traina-Dorge, V. L., Carr, J. K., Bailey-Wilson, J. E., Elston, R. C., Taylor, B. A., and Cohen, J. C. (1985). Cellular genes in the mouse regulate in trans the expression of endogenous mouse mammary tumor viruses, *Genetics* 111, 597–615.

Varmus, H. E. (1985). Viruses, genes, and cancer. I. The discovery of cellular oncogenes and their role in neoplasia, *Cancer* 55, 2324–8.

Varmus, H. E., Cohen, J. C., Shank, P. R., Ringold, G. M., Yamamoto, K. R., Cardiff, R., and Morris, V. L. (1978). The endogenous and acquired proviruses of mouse mammary tumor virus. pp. 161–79, In: Stevens Jg, et al., ed. Persistent viruses. New York, Academic Press. 11: 161–79.

Vogetseder, W., Denner, J., Boller, K., Kurth, R., and Dierich, M. P. (1995). Human endogenous retrovirus K does not encode mouse mammary tumor virus-related antigens in human breast carcinomas *AIDS Res Hum Retroviruses* 11, 869–72.

Wang, Y., Go, V., Holland, J. F., Melana, S. M., and Pogo, B. G. (1998) Expression of mouse mammary tumor virus-like env gene sequences in human breast cancer. *Clin. Cancer Res.* 4, 2565–2568.

Wang, Y., Holland, J. F., Bleiweiss, I. J., Melana, S., Liu, X., Pelisson, I., Cantarella, A., stellrecht, K., Mani, S., and Pogo, B. G. (1995). Detection of mammary tumor virus env gene-like sequences in human breast cancer. *Cancer Res.* 55, 5173–5179.

Ziegler, J. (1997). An unlikely link? Researchers probe viral role in breast cancer. *J Natl Cancer Inst.* 89, 608–10.

What is claimed is:

1. An isolated DNA molecule comprising:
   a) a DNA fragment having at least 99% identity with SEQ ID NO: 2, 3, 4, 5, 7, 8, 21, 25, or 27; or
   b) a DNA fragment identical with one or more of the following: at least 340 contiguous bases of SEQ ID NO:2, at least 150 contiguous nucleotides of the sequence represented by nucleotides 1–380 of SEQ ID NO:3, at least 140 contiguous nucleotides of the sequence represented by nucleotides 1–400 of SEQ ID NO:4, at least 130 contiguous nucleotides of the sequence represented by nucleotides 1–360 of SEQ ID NO:5, at least 130 contiguous nucleotides of SEQ ID NO:6, at least 140 contiguous nucleotides of the sequence represented by nucleotides 1–380 of SEQ ID NO:7, at least 210 contiguous nucleotides of the sequence represented by nucleotides 20–462 of SEQ ID NO:8, at least 160 contiguous nucleotides of the sequence represented by nucleotides 97–462 of SEQ ID NO:21, at least 170 contiguous nucleotides of SEQ ID NO:23, at least 100 contiguous nucleotides of the sequence represented by nucleotides 337–462 of SEQ ID NO:25, at least 300 contiguous nucleotides of the sequence represented by nucleotides 85–462 of SEQ ID NO:27, or at least 200 contiguous nucleotides of SEQ ID NO:29.

2. The isolated DNA molecule of claim 1 which comprises SEQ ID NO: 2, 3, 4, 5, 6, 7, 8, 21, 23, 25, 27, or 29.

3. The isolated DNA molecule of claim 1 wherein the DNA sequence is from human, rhesus macaque, or cat.

4. The isolated DNA molecule of claim 1, further comprising a detection moiety.

5. The isolated DNA molecule of claim 1, which is suspended or dissolved in a diluent.

6. The isolated DNA molecule of claim 5 wherein the diluent is a buffered aqueous solution.

7. The isolated DNA molecule of claim 5 wherein the DNA is present at a concentration of from about 0.1 ng/µl to 100 µg/µl.

8. A purified polypeptide encoded by a DNA molecule comprising:
   a) a DNA fragment having at least 99% identity with SEQ ID NO: 2, 3, 4, 5, 7, 8, 21, 25, or 27; or
   b) a DNA fragment identical with one or more of the following: at least 340 contiguous bases of SEQ ID NO:2, at least 150 contiguous nucleotides of the sequence represented by nucleotides 1–380 of SEQ ID NO:3, at least 140 contiguous nucleotides of the sequence represented by nucleotides 1–400 of SEQ ID NO:4, at least 130 contiguous nucleotides of the sequence represented by nucleotides 1–360 of SEQ ID NO:5, at least 130 contiguous nucleotides of SEQ ID NO:6, at least 140 contiguous nucleotides of the sequence represented by nucleotides 1–380 of SEQ ID NO:7, at least 210 contiguous nucleotides of the sequence represented by nucleotides 20–462 of SEQ ID NO:8, at least 160 contiguous nucleotides of the sequence represented by nucleotides 97–462 of SEQ ID NO:21, at least 170 contiguous nucleotides of SEQ ID NO:23, at least 100 contiguous nucleotides of the sequence represented by nucleotides 337–462 of SEQ ID NO:25, at least 300 contiguous nucleotides of the sequence represented by nucleotides 85–462 of SEQ ID NO:27, or at least 200 contiguous nucleotides of SEQ ID NO:29.

9. The purified polypeptide of claim 8 which is SEQ ID NO: 12, 13, 14, 15, 16, 17, 18, 22, 24, 26, 28, or 30.

10. The purified polypeptide of claim 8 which is present in a pharmaceutical composition.

11. An isolated antibody which specifically recognizes a polypeptide encoded by a DNA molecule comprising:
   a) a DNA fragment having at least 99% identity with SEQ ID NO: 2, 3, 4, 5, 7, 8, 21, 25, or 27; or
   b) a DNA fragment identical with one or more of the following: at least 340 contiguous bases of SEQ ID NO:2, at least 150 contiguous nucleotides of the sequence represented by nucleotides 1–380 of SEQ ID NO:3, at least 140 contiguous nucleotides of the sequence represented by nucleotides 1–400 of SEQ ID NO:4, at least 130 contiguous nucleotides of the sequence represented by nucleotides 1–360 of SEQ ID NO:5, at least 130 contiguous nucleotides of SEQ ID NO:6, at least 140 contiguous nucleotides of the sequence represented by nucleotides 1–380 of SEQ ID NO:7, at least 210 contiguous nucleotides of the sequence represented by nucleotides 20–462 of SEQ ID NO:8, at least 160 contiguous nucleotides of the sequence represented by nucleotides 97–462 of SEQ ID NO:21, at least 170 contiguous nucleotides of SEQ ID NO:23, at least 100 contiguous nucleotides of the sequence represented by nucleotides 337–462 of SEQ ID NO:25, at least 300 contiguous nucleotides of the sequence represented by nucleotides 85–462 of SEQ ID NO:27, or at least 200 contiguous nucleotides of SEQ ID NO:29;
wherein said antibody was generated using said polypeptide.

12. The antibody of claim 11 which is a monoclonal antibody.

13. An RNA corresponding to a DNA molecule comprising a:
   a) a DNA fragment having at least 99% identity with SEQ ID NO: 2, 3, 4, 5, 7, 8, 21, 25, or 27; or
   b) a DNA fragment identical with one or more of the following: at least 340 contiguous bases of SEQ ID NO:2, at least 150 contiguous nucleotides of the sequence represented by nucleotides 1–380 of SEQ ID NO:3, at least 140 contiguous nucleotides of the sequence represented by nucleotides 1–400 of SEQ ID NO:4, at least 130 contiguous nucleotides of the sequence represented by nucleotides 1–360 of SEQ ID NO:5, at least 130 contiguous nucleotides of SEQ ID NO:6, at least 140 contiguous nucleotides of the sequence represented by nucleotides 1–380 of SEQ ID NO:7, at least 210 contiguous nucleotides of the sequence represented by nucleotides 20–462 of SEQ ID NO:8, at least 160 contiguous nucleotides of the sequence represented by nucleotides 97–462 of SEQ ID NO:21, at least 170 contiguous nucleotides of SEQ ID NO:23, at least 100 contiguous nucleotides of the sequence represented by nucleotides 337–462 of SEQ ID NO:25, at least 300 contiguous nucleotides of the sequence represented by nucleotides 85–462 of SEQ ID NO:27, or at least 200 contiguous nucleotides of SEQ ID NO:29.

14. The isolated DNA molecule of claim 1 which is incorporated in a vector, wherein said DNA sequence is under the transcriptional control of a heterologous promoter.

15. The vector of claim 14 which is capable of expressing the DNA sequence in at least one of the following cell types: insect cells, bacterial cells, avian cells, yeast cells, or mammalian cells.

16. The vector of claim 14 wherein said vector is capable of episomal replication or chromosomal integration in at least one of the following cell types: insect cells, bacterial cells, avian cells, yeast cells, or mammalian cells.

17. A method for the detecting the presence of a mammary tumor viral DNA comprising the steps of:
   i) obtaining a biological sample suspected of containing DNA which comprises a sequence molecule a DNA molecule comprising:
      a) a DNA fragment having at least 99% identity with SEQ ID NO: 2, 3, 4, 5, 7, 8, 21, 25, or 27; or
      b) a DNA fragment identical with one or more of the following: at least 340 contiguous bases of SEQ ID NO:2, at least 150 contiguous nucleotides of the sequence represented by nucleotides 1–380 of SEQ ID NO:3, at least 140 contiguous nucleotides of the sequence represented by nucleotides 1–400 of SEQ ID NO:4, at least 130 contiguous nucleotides of the sequence represented by nucleotides 1–360 of SEQ ID NO:5, at least 130 contiguous nucleotides of SEQ ID NO:6, at least 140 contiguous nucleotides of the sequence represented by nucleotides 1–380 of SEQ ID NO:7, at least 210 contiguous nucleotides of the sequence represented by nucleotides 20–462 of SEQ ID NO:8, at least 160 contiguous nucleotides of the sequence represented by nucleotides 97–462 of SEQ ID NO:21, at least 170 contiguous nucleotides of SEQ ID NO:23, at least 100 contiguous nucleotides of the sequence represented by nucleotides 337–462 of SEQ ID NO:25, at least 300 contiguous nucleotides of the sequence represented by nucleotides 85–462 of SEQ ID NO:27, or at least 200 contiguous nucleotides of SEQ ID NO:29;
   ii) carrying out a polymerase chain reaction to amplify the suspected DNA sequence as defined in step i) to produce amplicons; and,
   iii) determining the sequence of, or otherwise characterizing, the amplicons produced in step ii) to determine whether or not the DNA sequence as defined in step i) is present in the sample.

18. The method of claim 17 wherein the biological sample is obtained from human, rhesus macaque, or cat.

19. A method of detecting the presence of antibodies which recode one or more mammary tumor virus polypeptides, the method comprising the steps of:
   i) obtaining a sample suspected of containing antibodies specific for mammary tumor viral antibodies;
   ii) obtaining at least one purified polypeptide encoded by a DNA molecule comprising:
      a) a DNA fragment having at least 99% identity with SEQ ID NO: 2, 3, 4, 5, 7, 8, 21, 25, or 27; or
      b) a DNA fragment identical with one or more of the following: at least 340 contiguous bases of SEQ ID NO:2, at least 150 contiguous nucleotides of the sequence represented by nucleotides 1–380 of SEQ ID NO:3, at least 140 contiguous nucleotides of the sequence represented by nucleotides 1–400 of SEQ ID NO:4, at least 130 contiguous nucleotides of the sequence represented by nucleotides 1–360 of SEQ ID NO:5, at least 130 contiguous nucleotides of SEQ ID NO:6, at least 140 contiguous nucleotides of the sequence represented by nucleotides 1–380 of SEQ ID NO:7, at least 210 contiguous nucleotides of the sequence represented by nucleotides 20–462 of SEQ ID NO:8, at least 160 contiguous nucleotides of the sequence represented by nucleotides 97–462 of SEQ ID NO:21, at least 170 contiguous nucleotides of SEQ ID NO:23, at least 100 contiguous nucleotides of the sequence represented by nucleotides 337–462 of SEQ ID NO:25, at least 300 contiguous nucleotides of the sequence represented by nucleotides 85–462 of SEQ ID NO:27, or at least 200 contiguous nucleotides of SEQ ID NO:29;

iii) performing an immunochemical analysis using the sample of step i) and the polypeptide of step ii); and, iv) analyzing the results of step iii) to determine whether or not antibodies which specifically interact with the peptide of step ii) are present in the sample.

20. The method of claim 19 wherein the immunochemical analysis of step iii) is a Western blot analysis.

21. The method of claim 19 wherein the immunochemical analysis of step iii) is enzyme-linked immunosorbant assay (ELISA) analysis.

22. The method of claim 19 wherein one or more of the polypeptides are derived from the env, or gag, gene and the antibodies are specific for one or more of the following polypeptides SEQ ID NO: 12, 13, 14, 15, 16, 17, 18, 22, 24, 26, 28, or30.

23. The method of claim 19 wherein the sample of step ii) comprises antibodies from a human, rhesus macaque, or cat.

24. A diagnostic kit for detecting DNA or RNA from a mammary tumor virus, said hit comprising a reagent comprising a DNA molecule comprising:

a) a DNA fragment having at least 99% identity with SEQ ID NO: 2, 3, 4, 5, 7, 8, 21, 25, or 27; or b) a DNA fragment identical with one or more of the following: at least 340 contiguous bases of SEQ ID NO:2, at least 150 contiguous nucleotides of the sequence represented by nucleotides 1–380 of SEQ ID NO:3, at least 140 contiguous nucleotides of the sequence represented by nucleotides 1–400 of SEQ ID NO:4, at least 130 contiguous nucleotides of the sequence represented by nucleotides 1–360 of SEQ ID NO:5, at least 130 contiguous nucleotides of SEQ ID NO:6, at least 140 contiguous nucleotides of the sequence represented by nucleotides 1–380 of SEQ ID NO:7, at least 210 contiguous nucleotides of the sequence represented by nucleotides 20–462 of SEQ ID NO:8, at least 160 contiguous nucleotides of the sequence represented by nucleotides 97–462 of SEQ ID NO:21, at least 170 contiguous nucleotides of SEQ ID NO:23, at least 100 contiguous nucleotides of the sequence represented by nucleotides 337–462 of SEQ ID NO:25, at least 300 contiguous nucleotides of the sequence represented by nucleotides 85–462 of SEQ ID NO:27, or at least 200 contiguous nucleotides of SEQ ID NO:29.

25. A diagnostic kit for detecting antibodies to mammary tumor virus, where said kit comprises a reagent comprising one or both of the following:

i) one or more polypeptides encoded by a DNA molecule comprising:

a) a DNA fragment having at least 99% identity with SEQ ID NO: 2, 3, 4, 5, 7, 8, 21, 25, or 27; or b) a DNA fragment identical with one or more of the following: at least 340 contiguous bases of SEQ ID NO:2, at least 150 contiguous nucleotides of the sequence represented by nucleotides 1–380 of SEQ ID NO:3, at least 140 contiguous nucleotides of the sequence represented by nucleotides 1–400 of SEQ ID NO:4, at least 130 contiguous nucleotides of the sequence represented by nucleotides 1–360 of SEQ ID NO:5, at least 130 contiguous nucleotides of SEQ ID NO:6, at least 140 contiguous nucleotides of the sequence represented by nucleotides 1–380 of SEQ ID NO:7, at least 210 contiguous nucleotides of the sequence represented by nucleotides 20–462 of SEQ ID NO:8, at least 160 contiguous nucleotides of the sequence represented by nucleotides 97–462 of SEQ ID NO:21, at least 170 contiguous nucleotides of SEQ ID NO:23, at least 100 contiguous nucleotides of the sequence represented by nucleotides 337–462 of SEQ ID NO:25, at least 300 contiguous nucleotides of the sequence represented by nucleotides 85–462 of SEQ ID NO:27, or at least 200 contiguous nucleotides of SEQ ID NO:29; or ii) an antibody specific for a polypeptide according to step i).

26. A method for the detection of MTV RNA in a sample which comprises the following steps:

i) obtaining an sample suspected of containing RNA which encoded by one or more DNA sequences comprising:

a) a DNA fragment having at least 99% identity with SEQ ID NO: 2, 3, 4, 5, 7, 8, 21, 25, or 27; or b) a DNA fragment identical with one or more of the following: at least 340 contiguous bases of SEQ ID NO:2, at least 150 contiguous nucleotides of the sequence represented by nucleotides 1–380 of SEQ ID NO:3, at least 140 contiguous nucleotides of the sequence represented by nucleotides 1–400 of SEQ ID NO:4, at least 130 contiguous nucleotides of the sequence represented by nucleotides 1–360 of SEQ ID NO:5, at least 130 contiguous nucleotides of SEQ ID NO:6, at least 140 contiguous nucleotides of the sequence represented by nucleotides 1–380 of SEQ ID NO7, at least 210 contiguous nucleotides of the sequence represented by nucleotides 20–462 of SEQ ID NO:8, at least 160 contiguous nucleotides of the sequence represented by nucleotides 97–462 of SEQ ID NO:2 1, at least 170 contiguous nucleotides of SEQ ID NO:23, at least 100 contiguous nucleotides of the sequence represented by nucleotides 337–462 of SEQ ID NO:25, at least 300 contiguous nucleotides of the sequence represented by nucleotides 85–462 of SEQ ID NO:27, or at least 200 contiguous nucleotides of SEQ ID NO:29; or ii) carrying out an RNAse protection assay (RPA); and, iii) analyzing the RPA results to determine whether RNA as defined in step i) is present in the sample and optionally quantitating said RNA.

* * * * *

UNITED STATES PATENT AND TRADEMARK OFFICE
CERTIFICATE OF CORRECTION

PATENT NO.    : 6,670,466 B1
DATED         : December 30, 2003
INVENTOR(S)   : Robert F. Garry It is certified that error appears in the above-identified patent and that said Letters Patent is hereby corrected as shown below:

<u>Column 44,</u>
Line 56, delete "recode" and replace with -- recognize -- therefor.

<u>Column 46,</u>
Line 49, delete "NO7" and insert -- NO:7 -- therefor.

Signed and Sealed this

Twenty-fourth Day of February, 2004

JON W. DUDAS
*Acting Director of the United States Patent and Trademark Office*

SEQUENCE LISTING

<160> NUMBER OF SEQ ID NOS: 30

<210> SEQ ID NO 1
<211> LENGTH: 461
<212> TYPE: DNA
<213> ORGANISM: Mouse mammary tumor virus

<400> SEQUENCE: 1

```
tcccttccct cgcctagtgt agatcagtca gatcagatta aaagcaaaaa ggatctattt      60
ggaaattata ctcccctgt caataaagag gttcatcgat ggtatgaagc aggatgggta     120
gaacctacat ggttctggga aaattctcct aaggatccca atgatagaga ttttactgct    180
ctagttcccc atacagaatt gtttcgctta gttgcagcct caagatatct tattctcaaa    240
aggccaggat ttcaagaaca tgacatgatt cctacatctg cctgtgttac ttacccttat    300
gccatattat taggattacc tcagctaata gatatagaga aagaggatc tacttttcat    360
atttcctgtt cttcttgtag attgactaat tgtttagatt cttctgccta cgactatgca    420
gcgatcatag tcaagaggcc gccatacgtg ctgctacctg t                        461
```

<210> SEQ ID NO 2
<211> LENGTH: 461
<212> TYPE: DNA
<213> ORGANISM: Human Mammary Tumor Virus

<400> SEQUENCE: 2

```
tcccttccct cgcctagtgt agatctgtca gatcagatta aaagcaaaaa ggatctattt      60
ggaaattata ctcccctgt caataaagag gttcatcgat ggtatgaagc aggatgggta    120
gaacctacat ggttctggga aaattctcct aaggatccca atgatagaga ttttactgct    180
ctagttcccc atacagaatt gtttcgctta gttgcagcct caagatatct tattctcaaa    240
aggccaggat ttcaagaaca tgacatgatt cctacatctg cctgtgttac ttacccttat    300
gccatattat taggattacc tcagctaata gatatagaaa aagaggatc tacttttcat    360
atttcctgtt cttcttgtag attgactaat tgtttagatt cttctgccta cgactatgca    420
gcgatcatag tcaagaaggc gccatatgtg ctgctacctg t                        461
```

<210> SEQ ID NO 3
<211> LENGTH: 461
<212> TYPE: DNA
<213> ORGANISM: Human Mammary Tumor Virus

<400> SEQUENCE: 3

```
tcccttccct cgcctagtgt agatcagtca gatcagatta aaaacaaaaa ggatctattt      60
ggaaattata ctcccctgt caataaagag gttcatcgat ggtatgaagc aggatgggta    120
gaacctactt ggttctggga aaattctcct aaggatccca atgatagaga ttttactgct    180
ctagttcccc atacagaatt gtttcgctta gttgcagcct caagacatct tattctcaaa    240
aagccaggat ttcaagaaca tgagatgatt cctacatctg cctgtgttac ttacccttat    300
```

```
gccatattat taggattacc tcagctaata gatatagaga aaagaggatc tactttcat    360
atttcctgtt cttcttgttg attgactaat tgtttagatt cttctgccta cgactatgca    420
gcgatcatag tcaagaggcc gccatacgtg ctgctacctg t                        461
```

<210> SEQ ID NO 4
<211> LENGTH: 461
<212> TYPE: DNA
<213> ORGANISM: Human Mammary Tumor Virus

<400> SEQUENCE: 4

```
tcccttccct cgcctagtat agaacagtca aatcagatta aaagcaaaaa ggatctactt    60
ggaaattata ctcccctgt caataaagag gttcatcgat ggtatgaagc aggatgggta    120
gaacctactt ggttctggga aaattctcct aaggatccca atgatagaga ttttactgct    180
ctagttcccc atacagaatt gtttcgctta gttgcagcct caagacatct tattctcaaa    240
aggccaggat ttcaagaaca tgagatgatt cctacatctg cctgtgttac ttacccttat    300
gccatattat taggattacc tcagctaata gatatagaga agagaggatc tactttcat    360
atttcctgtt cttcttgtag attgactaat tgtttagact cttctgccta cgactatgca    420
gcgatcatag tcaagaggcc gccatacgtg ctgctacctg t                        461
```

<210> SEQ ID NO 5
<211> LENGTH: 461
<212> TYPE: DNA
<213> ORGANISM: Rhesus Mammary Tumor Virus

<400> SEQUENCE: 5

```
tcccttccct cgcctagtgt agatcagtca aatcagatta aaagcaaaaa ggatctattt    60
ggaaattata ctcccctgt caataaagag gttcatcgat ggtatgaagc aggatgggta    120
gaacctactt ggttctggga aaattctcct aaagatccca atgatagaga ttttactgct    180
ctagttcccc atacagaatt gtttcgctta gttgcagcct caagacatct tattctcaaa    240
aagccaggat ttcaagaaca tgagatgatt cctacatctg cctgtgttac ttacccttat    300
gccatattat taggattacc tcagctaata gatatagaga aaagaggatc tactttcat    360
atttcctgtt cttcttgtag attgactaat tgtttagatt cttctgccta cgactatgca    420
gcgatcatag tcaagaggcc gccatacgtg ctgctacctg t                        461
```

<210> SEQ ID NO 6
<211> LENGTH: 461
<212> TYPE: DNA
<213> ORGANISM: Rhesus Mammary Tumor Virus

<400> SEQUENCE: 6

```
tcccttccct cgcctagtgt agatcagtca aatcagatta aaagcaaaaa ggatctattt    60
ggaaattata ctcccctgt caataaagag gttcatcgat ggtatgaagc aggatgggta    120
gaacctactt ggttctggga aaattctcct aaagatccca atgatagaga ttttactgct    180
ctagttcccc atacagaatt gtttcgctta gttgcagcct caagacatct tattctcaaa    240
aagccaggat ttcaagaaca tgagatgatt cctacatctg cctgtgttac ttacccttat    300
gccatattat taggattacc tcagctaata gatatagaga aaagaggatc tactttcat    360
atttcctgtt cttcttgtag accgactaat tgtttagatt cttctgccta cgactatgca    420
gcgatcatag tcaagaggcc gccatacgtg ctgctacctg t                        461
```

<210> SEQ ID NO 7
<211> LENGTH: 461
<212> TYPE: DNA
<213> ORGANISM: Cat Mammary Tumor Virus

<400> SEQUENCE: 7

```
tcccttccct cgcctagtgt agaacagtca gatcagatta aaagcaaaaa ggatctactt      60
ggaaattata ctcccctgt caataaagag gttcatcgat ggtatgaagc aggatgggta     120
gaacctacat ggttctggga aaattctcct aaggatccca atgatagaga ttttattgct    180
ctagttcccc atacagaatt gtttcgctta gttgcagcct caagacatct tattctcaaa    240
aagccaggat ttcaagaaca taagatgatt cctacatctg cctgtgttac ttacccttat    300
gccatattat taggattacc tcagctaata gatatagaga aaagaggatc tacttttcat    360
atttcctgtt cttcttgtag attgactaat tgtttagatt cttctgccta cgactatgca    420
gcgatcatag tcaagaggcc gccatacgtg ctgctacctg t                        461
```

<210> SEQ ID NO 8
<211> LENGTH: 461
<212> TYPE: DNA
<213> ORGANISM: Cat Mammary Tumor Virus

<400> SEQUENCE: 8

```
tcccttccct cgcctagtgt agaacagtca gatcagatta aaagcaaaaa ggatctactt      60
ggaaattata ctcccctgt caataaagag gttcatcgat ggtatgaagc aggatgggta     120
gaacctacat ggttctggga aaattctcct aaggatccca atgatagaga ttttactgct    180
ctagttcccc atacagaatt gtttcgctta gttgcagcct caagacatct tattctcaaa    240
aagccaggat ttcaagaaca taagatgatt cctacatctg cctgtgttac ttacccttat    300
gccatattat taagattacc tcagctaata gatatagaga aaagaggatc tacttttcat    360
atttcctgtt cttcttgtag attgactaat tgtttagatt cttctgccta cgactatgca    420
gcgatcatag tcaagaggcc gccatacgtg ctgctacctg t                        461
```

<210> SEQ ID NO 9
<211> LENGTH: 104
<212> TYPE: DNA
<213> ORGANISM: Mouse mammary tumor virus

<400> SEQUENCE: 9

```
atgatgccga gaggagaagg gtcagatata ttgatcaagc aattggcatg ggaaaatgca      60
aattcattgt gtcaggatct catccgccca atacgaaaaa cagg                     104
```

<210> SEQ ID NO 10
<211> LENGTH: 104
<212> TYPE: DNA
<213> ORGANISM: Cat Mammary Tumor Virus

<400> SEQUENCE: 10

```
atgatgccga gaggagaagg gtcagatata ttgatcaaac aattggcgta aaaaaatgca      60
aattcattgt gccaagatct tatccgtcca atacgaaaaa cagg                     104
```

<210> SEQ ID NO 11
<211> LENGTH: 153
<212> TYPE: PRT
<213> ORGANISM: Mouse mammary tumor virus

<400> SEQUENCE: 11

```
Ser Leu Pro Ser Pro Ser Val Asp Gln Ser Asp Gln Ile Lys Ser Lys
1               5                   10                  15

Lys Asp Leu Phe Gly Asn Tyr Thr Pro Pro Val Asn Lys Glu Val His
            20                  25                  30

Arg Trp Tyr Glu Ala Gly Trp Val Glu Pro Thr Trp Phe Trp Glu Asn
        35                  40                  45

Ser Pro Lys Asp Pro Asn Asp Arg Asp Phe Thr Ala Leu Val Pro His
    50                  55                  60

Thr Glu Leu Phe Arg Leu Val Ala Ala Ser Arg Tyr Leu Ile Leu Lys
65                  70                  75                  80

Arg Pro Gly Phe Gln Glu His Asp Met Ile Pro Thr Ser Ala Cys Val
                85                  90                  95

Thr Tyr Pro Tyr Ala Ile Leu Leu Gly Leu Pro Gln Leu Ile Asp Ile
                100                 105                 110

Glu Lys Arg Gly Ser Thr Phe His Ile Ser Cys Ser Ser Cys Arg Leu
                115                 120                 125

Thr Asn Cys Leu Asp Ser Ser Ala Tyr Asp Tyr Ala Ala Ile Ile Val
            130                 135                 140

Lys Arg Pro Pro Tyr Val Leu Leu Pro
145                 150

<210> SEQ ID NO 12
<211> LENGTH: 153
<212> TYPE: PRT
<213> ORGANISM: Human Mammary Tumor Virus

<400> SEQUENCE: 12

Ser Leu Pro Ser Pro Ser Val Asp Leu Ser Asp Gln Ile Lys Ser Lys
1               5                   10                  15

Lys Asp Leu Phe Gly Asn Tyr Thr Pro Pro Val Asn Lys Glu Val His
            20                  25                  30

Arg Trp Tyr Glu Ala Gly Trp Val Glu Pro Thr Trp Phe Trp Glu Asn
        35                  40                  45

Ser Pro Lys Asp Pro Asn Asp Arg Asp Phe Thr Ala Leu Val Pro His
    50                  55                  60

Thr Glu Leu Phe Arg Leu Val Ala Ala Ser Arg Tyr Leu Ile Leu Lys
65                  70                  75                  80

Arg Pro Gly Phe Gln Glu His Asp Met Ile Pro Thr Ser Ala Cys Val
                85                  90                  95

Thr Tyr Pro Tyr Ala Ile Leu Leu Gly Leu Pro Gln Leu Ile Asp Ile
                100                 105                 110

Glu Lys Arg Gly Ser Thr Phe His Ile Ser Cys Ser Ser Cys Arg Leu
                115                 120                 125

Thr Asn Cys Leu Asp Ser Ser Ala Tyr Asp Tyr Ala Ala Ile Ile Val
            130                 135                 140

Lys Lys Ala Pro Tyr Val Leu Leu Pro
145                 150

<210> SEQ ID NO 13
<211> LENGTH: 152
<212> TYPE: PRT
<213> ORGANISM: Human Mammary Tumor Virus

<400> SEQUENCE: 13

Ser Leu Pro Ser Pro Ser Val Asp Gln Ser Asp Gln Ile Lys Asn Lys
1               5                   10                  15
```

Lys Asp Leu Phe Gly Asn Tyr Thr Pro Pro Val Asn Lys Glu Val His
            20                  25                  30

Arg Trp Tyr Glu Ala Gly Trp Val Glu Pro Thr Trp Phe Trp Glu Asn
            35                  40                  45

Ser Pro Lys Asp Pro Asn Asp Arg Asp Phe Thr Ala Leu Val Pro His
 50                      55                  60

Thr Glu Leu Phe Arg Leu Val Ala Ala Ser Arg His Leu Ile Leu Lys
 65                  70                  75                  80

Lys Pro Gly Phe Gln Glu His Glu Met Ile Pro Thr Ser Ala Cys Val
                85                  90                  95

Thr Tyr Pro Tyr Ala Ile Leu Leu Gly Leu Pro Gln Leu Ile Asp Ile
            100                 105                 110

Glu Lys Arg Gly Ser Thr Phe His Ile Ser Cys Ser Ser Cys Leu Thr
            115                 120                 125

Asn Cys Leu Asp Ser Ser Ala Tyr Asp Tyr Ala Ala Ile Ile Val Lys
        130                 135                 140

Arg Pro Pro Tyr Val Leu Leu Pro
145                 150

<210> SEQ ID NO 14
<211> LENGTH: 153
<212> TYPE: PRT
<213> ORGANISM: Human Mammary Tumor Virus

<400> SEQUENCE: 14

Ser Leu Pro Ser Pro Ser Ile Glu Gln Ser Asn Gln Ile Lys Ser Lys
1               5                   10                  15

Lys Asp Leu Leu Gly Asn Tyr Thr Pro Pro Val Asn Lys Glu Val His
            20                  25                  30

Arg Trp Tyr Glu Ala Gly Trp Val Glu Pro Thr Trp Phe Trp Glu Asn
            35                  40                  45

Ser Pro Lys Asp Pro Asn Asp Arg Asp Phe Thr Ala Leu Val Pro His
 50                      55                  60

Thr Glu Leu Phe Arg Leu Val Ala Ala Ser Arg His Leu Ile Leu Lys
 65                  70                  75                  80

Arg Pro Gly Phe Gln Glu His Glu Met Ile Pro Thr Ser Ala Cys Val
                85                  90                  95

Thr Tyr Pro Tyr Ala Ile Leu Leu Gly Leu Pro Gln Leu Ile Asp Ile
            100                 105                 110

Glu Lys Arg Gly Ser Thr Phe His Ile Ser Cys Ser Ser Cys Arg Leu
            115                 120                 125

Thr Asn Cys Leu Asp Ser Ser Ala Tyr Asp Tyr Ala Ala Ile Ile Val
        130                 135                 140

Lys Arg Pro Pro Tyr Val Leu Leu Pro
145                 150

<210> SEQ ID NO 15
<211> LENGTH: 153
<212> TYPE: PRT
<213> ORGANISM: Rhesus Mammary Tumor Virus

<400> SEQUENCE: 15

Ser Leu Pro Ser Pro Ser Val Asp Gln Ser Asn Gln Ile Lys Ser Lys
1               5                   10                  15

Lys Asp Leu Phe Gly Asn Tyr Thr Pro Pro Val Asn Lys Glu Val His
            20                  25                  30

```
Arg Trp Tyr Glu Ala Gly Trp Val Glu Pro Thr Trp Phe Trp Glu Asn
         35                  40                  45

Ser Pro Lys Asp Pro Asn Asp Arg Asp Phe Thr Ala Leu Val Pro His
 50                  55                  60

Thr Glu Leu Phe Arg Leu Val Ala Ala Ser Arg His Leu Ile Leu Lys
 65                  70                  75                  80

Lys Pro Gly Phe Gln Glu His Glu Met Ile Pro Thr Ser Ala Cys Val
                 85                  90                  95

Thr Tyr Pro Tyr Ala Ile Leu Leu Gly Leu Pro Gln Leu Ile Asp Ile
                 100                 105                 110

Glu Lys Arg Gly Ser Thr Phe His Ile Ser Cys Ser Ser Cys Arg Leu
             115                 120                 125

Thr Asn Cys Leu Asp Ser Ser Ala Tyr Asp Tyr Ala Ala Ile Ile Val
 130                 135                 140

Lys Arg Pro Pro Tyr Val Leu Leu Pro
145                 150

<210> SEQ ID NO 16
<211> LENGTH: 153
<212> TYPE: PRT
<213> ORGANISM: Rhesus Mammary Tumor Virus

<400> SEQUENCE: 16

Ser Leu Pro Ser Pro Ser Val Asp Gln Ser Asn Gln Ile Lys Ser Lys
 1               5                   10                  15

Lys Asp Leu Phe Gly Asn Tyr Thr Pro Pro Val Asn Lys Glu Val His
                 20                  25                  30

Arg Trp Tyr Glu Ala Gly Trp Val Glu Pro Thr Trp Phe Trp Glu Asn
         35                  40                  45

Ser Pro Lys Asp Pro Asn Asp Arg Asp Phe Thr Ala Leu Val Pro His
 50                  55                  60

Thr Glu Leu Phe Arg Leu Val Ala Ala Ser Arg His Leu Ile Leu Lys
 65                  70                  75                  80

Lys Pro Gly Phe Gln Glu His Glu Met Ile Pro Thr Ser Ala Cys Val
                 85                  90                  95

Thr Tyr Pro Tyr Ala Ile Leu Leu Gly Leu Pro Gln Leu Ile Asp Ile
                 100                 105                 110

Glu Lys Arg Gly Ser Thr Phe His Ile Ser Cys Ser Ser Cys Arg Pro
             115                 120                 125

Thr Asn Cys Leu Asp Ser Ser Ala Tyr Asp Tyr Ala Ala Ile Ile Val
 130                 135                 140

Lys Arg Pro Pro Tyr Val Leu Leu Pro
145                 150

<210> SEQ ID NO 17
<211> LENGTH: 153
<212> TYPE: PRT
<213> ORGANISM: Cat Mammary Tumor Virus

<400> SEQUENCE: 17

Ser Leu Pro Ser Pro Ser Val Glu Gln Ser Asp Gln Ile Lys Ser Lys
 1               5                   10                  15

Lys Asp Leu Leu Gly Asn Tyr Thr Pro Pro Val Asn Lys Glu Val His
                 20                  25                  30

Arg Trp Tyr Glu Ala Gly Trp Val Glu Pro Thr Trp Phe Trp Glu Asn
         35                  40                  45
```

```
Ser Pro Lys Asp Pro Asn Asp Arg Asp Phe Thr Ala Leu Val Pro His
    50                  55                  60

Thr Glu Leu Phe Arg Leu Val Ala Ala Ser Arg His Leu Ile Leu Lys
65                  70                  75                  80

Lys Pro Gly Phe Gln Glu His Lys Met Ile Pro Thr Ser Ala Cys Val
                85                  90                  95

Thr Tyr Pro Tyr Ala Ile Leu Leu Arg Leu Pro Gln Leu Ile Asp Ile
                100                 105                 110

Glu Lys Arg Gly Ser Thr Phe His Ile Ser Cys Ser Cys Arg Leu
                115                 120                 125

Thr Asn Cys Leu Asp Ser Ser Ala Tyr Asp Tyr Ala Ala Ile Ile Val
    130                 135                 140

Lys Arg Pro Pro Tyr Val Leu Leu Pro
145                 150

<210> SEQ ID NO 18
<211> LENGTH: 153
<212> TYPE: PRT
<213> ORGANISM: Cat Mammary Tumor Virus

<400> SEQUENCE: 18

Ser Leu Pro Ser Pro Ser Val Glu Gln Ser Asp Gln Ile Lys Ser Lys
1               5                   10                  15

Lys Asp Leu Leu Gly Asn Tyr Thr Pro Pro Val Asn Lys Glu Val His
                20                  25                  30

Arg Trp Tyr Glu Ala Gly Trp Val Glu Pro Thr Trp Phe Trp Glu Asn
                35                  40                  45

Ser Pro Lys Asp Pro Asn Asp Arg Asp Phe Thr Ala Leu Val Pro His
    50                  55                  60

Thr Glu Leu Phe Arg Leu Val Ala Ala Ser Arg His Leu Ile Leu Lys
65                  70                  75                  80

Lys Pro Gly Phe Gln Glu His Lys Met Ile Pro Thr Ser Ala Cys Val
                85                  90                  95

Thr Tyr Pro Tyr Ala Ile Leu Leu Arg Leu Pro Gln Leu Ile Asp Ile
                100                 105                 110

Glu Lys Arg Gly Ser Thr Phe His Ile Ser Cys Ser Cys Arg Leu
                115                 120                 125

Thr Asn Cys Leu Asp Ser Ser Ala Tyr Asp Tyr Ala Ala Ile Ile Val
    130                 135                 140

Lys Arg Pro Pro Tyr Val Leu Leu Pro
145                 150

<210> SEQ ID NO 19
<211> LENGTH: 35
<212> TYPE: PRT
<213> ORGANISM: Mouse mammary tumor virus

<400> SEQUENCE: 19

Met Met Pro Arg Gly Glu Gly Ser Asp Ile Leu Ile Lys Gln Leu Ala
1               5                   10                  15

Trp Glu Lys Cys Lys Phe Ile Val Ser Gly Ser His Pro Asn Thr
                20                  25                  30

Lys Asn Arg
        35

<210> SEQ ID NO 20
```

```
<211> LENGTH: 35
<212> TYPE: PRT
<213> ORGANISM: Cat Mammary Tumor Virus

<400> SEQUENCE: 20

Met Met Pro Arg Gly Glu Gly Ser Asp Ile Leu Ile Lys Gln Leu Ala
 1               5                  10                  15

Tyr Lys Lys Cys Lys Phe Ile Val Pro Arg Ser Tyr Pro Ser Asn Thr
            20                  25                  30

Lys Asn Arg
       35

<210> SEQ ID NO 21
<211> LENGTH: 460
<212> TYPE: DNA
<213> ORGANISM: Human Mammary Tumor Virus

<400> SEQUENCE: 21
tcccttccct cgcctagtgt agatcagtca gatcagatta aaagcaaaag gatctatttg      60
gaaattatac tcccctgtc aataaagagg ttcatcggtg gtatgaagca ggatgggtag     120
aacctacatg gttctgggaa aattctccta aggatcccaa tgatagagat tttactgctc     180
tagttcccca tacagaattg tttcgcttag ttgcagcctc aagatatctt attctcaaaa     240
ggccaggatt tcaaggacat gacatgattc ctacatctgc ctgtgttact tacccttatg     300
ccatattatt aggattacct cagctaatag atatagaaaa aagaggatct acttttcata     360
tttcctgttc ttcttgtaaa ttgactaatt gtttagattc ttctgcctac gactatgcag     420
cgatcatagt caagaaggcg ccatatgtgc tgctacctgt                           460

<210> SEQ ID NO 22
<211> LENGTH: 38
<212> TYPE: PRT
<213> ORGANISM: Human Mammary Tumor Virus

<400> SEQUENCE: 22

Ser Leu Pro Ser Pro Ser Val Asp Gln Ser Asp Gln Ile Lys Ser Lys
 1               5                  10                  15

Arg Ile Tyr Leu Glu Ile Ile Leu Pro Leu Ser Ile Lys Phe Ile Gly
            20                  25                  30

Gly Met Lys Gln Asp Gly
       35

<210> SEQ ID NO 23
<211> LENGTH: 461
<212> TYPE: DNA
<213> ORGANISM: Human Mammary Tumor Virus

<400> SEQUENCE: 23
tcccttccct cgcctagtgt agatcagtca gatcagatta aaagcaaaaa ggatctattt      60
ggaaattata ctcccctgt caataaaggg gttcatcgat ggtatgaagc aggatgggta     120
gagcctacat ggttctggga aaattctcct aaggatccca atgatagaga ttttactgct     180
ctagttcccc atacagaatt gtttcgctta gttgcagcct caagatatct tattctcaaa     240
aggccaggat tcaaggaca tgacatgatt cctacatctg cctgtgttac ttacccttat     300
gccatattat taggattacc tcagctaata gatatagaaa aagaggatc tacttttcat     360
atttcctgtt cttcttgtaa attgactaat tgtttagat cttctgccta cgaatatgca     420
gcgatcatag tcaagaaggc gccatatgtg ctgctacctg t                         461
```

<210> SEQ ID NO 24
<211> LENGTH: 153
<212> TYPE: PRT
<213> ORGANISM: Human Mammary Tumor Virus

<400> SEQUENCE: 24

```
Ser Leu Pro Ser Pro Ser Val Asp Leu Ser Asp Gln Ile Lys Ser Lys
1               5                   10                  15

Lys Asp Leu Phe Gly Asn Tyr Thr Pro Pro Val Asn Lys Glu Val His
            20                  25                  30

Arg Trp Tyr Glu Ala Gly Trp Val Glu Pro Thr Trp Phe Trp Glu Asn
        35                  40                  45

Ser Pro Lys Asp Pro Asn Asp Arg Asp Phe Thr Ala Leu Val Pro His
    50                  55                  60

Thr Glu Leu Phe Arg Leu Val Ala Ala Ser Arg Tyr Leu Ile Leu Lys
65                  70                  75                  80

Arg Pro Gly Phe Gln Glu His Asp Met Ile Pro Thr Ser Ala Cys Val
                85                  90                  95

Thr Tyr Pro Tyr Ala Ile Leu Leu Gly Leu Pro Gln Leu Ile Asp Ile
            100                 105                 110

Glu Lys Arg Gly Ser Thr Phe His Ile Ser Cys Ser Cys Arg Leu
        115                 120                 125

Thr Asn Cys Leu Asp Ser Ser Ala Tyr Asp Tyr Ala Ala Ile Ile Val
    130                 135                 140

Lys Lys Ala Pro Tyr Val Leu Leu Pro
145                 150
```

<210> SEQ ID NO 25
<211> LENGTH: 461
<212> TYPE: DNA
<213> ORGANISM: Human Mammary Tumor Virus

<400> SEQUENCE: 25

```
tcccttccct cgcctagtgt agatcagtca gatcagatta aaagcaaaaa ggatctattt      60
ggaaattata ctcccctgt caataaagag gttcatcgat ggtatgaagc aggatgggta     120
gaacctacat ggttctggga aaattctcct aaggatccca atgatagaga ttttactgct    180
ctagttcccc atacagaatt gtttcgctta gttgcagcct caagatatct tattctcaaa    240
aggccaggat tcaagaaca tgacatgatt cctacatctg cctgtgttac ttacccttat     300
gccatattat taggattacc tcagctaata gatatagaaa aaagaggatc tactttcat    360
atttcctgtt cttcttgtag attgactaat tgtttagatt cttctgccta cgactatgca    420
gcgatcatag tcaagaaggc gccatatgtg ctgctacctg t                         461
```

<210> SEQ ID NO 26
<211> LENGTH: 153
<212> TYPE: PRT
<213> ORGANISM: Human Mammary Tumor Virus

<400> SEQUENCE: 26

```
Ser Leu Pro Ser Pro Ser Val Asp Leu Ser Asp Gln Ile Lys Ser Lys
1               5                   10                  15

Lys Asp Leu Phe Gly Asn Tyr Thr Pro Pro Val Asn Lys Gly Val His
            20                  25                  30

Arg Trp Tyr Glu Ala Gly Trp Val Glu Pro Thr Trp Phe Trp Glu Asn
        35                  40                  45
```

Ser Pro Lys Asp Pro Asn Asp Arg Asp Phe Thr Ala Leu Val Pro His
            50                  55                  60

Thr Glu Leu Phe Arg Leu Val Ala Ala Ser Arg Tyr Leu Ile Leu Lys
 65                  70                  75                  80

Arg Pro Gly Phe Gln Glu His Asp Met Ile Pro Thr Ser Ala Cys Val
                 85                  90                  95

Thr Tyr Pro Tyr Ala Ile Leu Leu Gly Leu Pro Gln Leu Ile Asp Ile
            100                 105                 110

Glu Lys Arg Gly Ser Thr Phe His Ile Ser Cys Ser Cys Arg Leu
            115                 120                 125

Thr Asn Cys Leu Asp Ser Ser Ala Tyr Asp Tyr Ala Ala Ile Ile Val
            130                 135                 140

Lys Lys Ala Pro Tyr Val Leu Leu Pro
145                 150

<210> SEQ ID NO 27
<211> LENGTH: 460
<212> TYPE: DNA
<213> ORGANISM: Human Mammary Tumor Virus

<400> SEQUENCE: 27
tcccttccct cgcctagtgt agatcagtca gatcagatta aaagcaaaaa ggatctattt     60
ggaaattata ctcccctgt caataaaggg gttcatcgat ggtatgaagc aggatgggta    120
gagcctacat ggttctggga aaattctcct aaggatccca atgatagaga ttttactgct    180
ctagttcccc atacagaatt gtttcgctta gttgcagcct caagatatct tattctcaaa    240
aggccaggat ttcaagaaca tgacatgatt cctacatctg cctgtgttac ttacccttat    300
gccatattat taggattacc tcagctaata gatatagaaa aagaagatc tactttttcat    360 atttcctgtt cttcttgtag attgactaat ttgtttagat cttctgccta cgaatatgca    420
gcgatcatag tcaagaaggg ccatatgtgc tgctacctgt                          460

<210> SEQ ID NO 28
<211> LENGTH: 152
<212> TYPE: PRT
<213> ORGANISM: Human Mammary Tumor Virus

<400> SEQUENCE: 28

Ser Leu Pro Ser Pro Ser Val Asp Leu Ser Asp Gln Ile Lys Ser Lys
  1               5                  10                  15

Lys Asp Leu Phe Gly Asn Tyr Thr Pro Pro Val Asn Lys Glu Val His
             20                  25                  30

Arg Trp Tyr Glu Ala Gly Trp Val Glu Pro Thr Trp Phe Trp Glu Asn
             35                  40                  45

Ser Pro Lys Asp Pro Asn Asp Arg Asp Phe Thr Ala Leu Val Pro His
            50                  55                  60

Thr Glu Leu Phe Arg Leu Val Ala Ala Ser Arg Tyr Leu Ile Leu Lys
 65                  70                  75                  80

Arg Pro Gly Phe Gln Glu His Asp Met Ile Pro Thr Ser Ala Cys Val
                 85                  90                  95

Thr Tyr Pro Tyr Ala Ile Leu Leu Gly Leu Pro Gln Leu Ile Asp Ile
            100                 105                 110

Glu Lys Arg Gly Ser Thr Phe His Ile Ser Cys Ser Cys Arg Leu
            115                 120                 125

Thr Asn Cys Leu Asp Ser Ser Ala Tyr Glu Tyr Ala Ala Ile Ile Val

-continued

```
                130              135              140
Lys Lys Gly His Met Cys Cys Leu
145                 150

<210> SEQ ID NO 29
<211> LENGTH: 461
<212> TYPE: DNA
<213> ORGANISM: Human Mammary Tumor Virus

<400> SEQUENCE: 29
tcccttccct cgcctagtgt agatcagtca gatcagatta aaaacaaaaa ggatctattt      60
ggaaattata ctccccctgt caataaagag gttcatcgat ggtatgaagc aggatgggta    120
gaacctactt gattctggga aaattctcct aaagatccca atgatagaga ttttactgct    180
ctagttcccc atacagaatt gttccgctta gttgcagcct caagacatct tattctcaaa    240
aagccaggat ttcaagaaga tgacatgatt cctacatctg cctgtgttac ttaccctat     300 gccatattat taggattacc tcagctaata gatatagaga aaagaggatc tacttttcat    360
atttcctgtt cttcttgtag attgactaat tgtttagatt cttctgccta cgactatgca    420
gcgatcatag tcaagaaggc gccatacgtg ctgctacctg t                        461

<210> SEQ ID NO 30
<211> LENGTH: 43
<212> TYPE: PRT
<213> ORGANISM: Human Mammary Tumor Virus

<400> SEQUENCE: 30

Ser Leu Pro Ser Pro Ser Val Asp Gln Ser Asp Gln Ile Lys Asn Lys
1               5                   10                  15

Lys Asp Leu Phe Gly Asn Tyr Thr Pro Pro Val Asn Lys Glu Val His
                20                  25                  30

Arg Trp Tyr Glu Ala Gly Trp Val Glu Pro Thr
            35                  40
```